United States Patent
Auth et al.

(10) Patent No.: US 7,257,450 B2
(45) Date of Patent: Aug. 14, 2007

(54) SYSTEMS AND METHODS FOR SECURING CARDIOVASCULAR TISSUE

(75) Inventors: David C. Auth, Kirkland, WA (US); Dean T. Corcoran, Bothell, WA (US); Mark A. Tempel, Sammamish, WA (US); Joseph E. Eichinger, Everett, WA (US)

(73) Assignee: CoAptus Medical Corporation, Redmond, WA (US)

( * ) Notice: Subject to any disclaimer, the term of this patent is extended or adjusted under 35 U.S.C. 154(b) by 228 days.

(21) Appl. No.: 11/004,634

(22) Filed: Dec. 2, 2004

(65) Prior Publication Data
US 2006/0122680 A1    Jun. 8, 2006

Related U.S. Application Data

(63) Continuation-in-part of application No. 10/754,790, filed on Jan. 8, 2004.

(60) Provisional application No. 60/474,055, filed on May 28, 2003, provisional application No. 60/447,760, filed on Feb. 13, 2003.

(51) Int. Cl.
*A61N 1/05*    (2006.01)
*A61N 1/18*    (2006.01)

(52) U.S. Cl. .................................................. 607/122
(58) Field of Classification Search ................. 607/122
See application file for complete search history.

(56) References Cited

U.S. PATENT DOCUMENTS

| | | |
|---|---|---|
| 2,582,628 A | 1/1952 | Halloran |
| 3,862,627 A | 1/1975 | Hans, Sr. |
| 4,273,127 A | 6/1981 | Auth et al. |
| 4,492,231 A | 1/1985 | Auth |
| 4,532,924 A | 8/1985 | Auth et al. |
| 4,556,065 A | 12/1985 | Hoffmann |
| 4,799,479 A | 1/1989 | Spears |

(Continued)

FOREIGN PATENT DOCUMENTS

WO    WO-87/04081 A1    7/1987

(Continued)

OTHER PUBLICATIONS

U.S. Appl. No. 11/004,634, Auth et al.

(Continued)

*Primary Examiner*—George Manuel
*Assistant Examiner*—Christopher A. Flory
(74) *Attorney, Agent, or Firm*—Perkins Coie LLP

(57) ABSTRACT

Methods and systems for securing tissues, e.g., cardiovascular tissues, are disclosed. A method in accordance with one embodiment of the invention includes inserting a portion of a catheter into an opening between a first portion of cardiovascular tissue and a second portion of cardiovascular tissue. The method can further include drawing the first and second portions of the cardiovascular tissue into contact with each other by drawing a vacuum in a region adjacent to the first and second portions of cardiovascular tissue via the catheter while the catheter is positioned between the first and second portions. The tissue portions can be fused by heating the tissue from within the opening, e.g., via radio frequency energy. This technique, and associated catheter system, can be used to close a patent foramen ovale or other openings in cardiovascular tissue.

37 Claims, 9 Drawing Sheets

U.S. PATENT DOCUMENTS

| | | |
|---|---|---|
| 4,813,926 A | 3/1989 | Kerwin |
| 4,822,348 A | 4/1989 | Casey |
| 4,832,048 A | 5/1989 | Cohen |
| 4,850,960 A | 7/1989 | Grayzel |
| 4,892,098 A | 1/1990 | Sauer |
| 4,929,246 A | 5/1990 | Sinofsky |
| 5,056,517 A | 10/1991 | Fenici |
| 5,071,417 A | 12/1991 | Sinofsky |
| 5,122,137 A | 6/1992 | Lennox |
| 5,156,613 A | 10/1992 | Sawyer |
| 5,207,670 A | 5/1993 | Sinofsky |
| 5,290,272 A | 3/1994 | Burstein et al. |
| 5,290,278 A | 3/1994 | Anderson |
| 5,298,224 A | 3/1994 | Plum |
| 5,300,065 A | 4/1994 | Anderson |
| 5,334,191 A | 8/1994 | Poppas et al. |
| 5,336,221 A | 8/1994 | Anderson |
| 5,364,389 A | 11/1994 | Anderson |
| 5,405,322 A | 4/1995 | Lennox et al. |
| 5,409,479 A | 4/1995 | Dew et al. |
| 5,409,481 A | 4/1995 | Poppas et al. |
| 5,421,338 A | 6/1995 | Crowley et al. |
| 5,451,235 A | 9/1995 | Lock et al. |
| 5,454,807 A | 10/1995 | Lennox et al. |
| 5,505,730 A | 4/1996 | Edwards |
| 5,507,744 A | 4/1996 | Tay et al. |
| 5,522,873 A | 6/1996 | Jackman et al. |
| 5,540,677 A | 7/1996 | Sinofsky |
| 5,545,195 A | 8/1996 | Lennox et al. |
| 5,569,239 A | 10/1996 | Sinofsky |
| 5,571,088 A | 11/1996 | Lennox et al. |
| 5,571,216 A | 11/1996 | Anderson |
| 5,575,772 A | 11/1996 | Lennox |
| 5,584,872 A | 12/1996 | LaFontaine et al. |
| 5,611,794 A | 3/1997 | Sauer et al. |
| 5,643,171 A | 7/1997 | Bradshaw et al. |
| 5,658,280 A | 8/1997 | Issa |
| 5,662,643 A | 9/1997 | Kung et al. |
| 5,662,647 A | 9/1997 | Crow et al. |
| 5,669,934 A | 9/1997 | Sawyer |
| 5,695,493 A | 12/1997 | Nakajima et al. |
| 5,702,421 A | 12/1997 | Schneidt |
| 5,709,224 A | 1/1998 | Behl et al. |
| 5,713,891 A | 2/1998 | Poppas |
| 5,725,512 A | 3/1998 | Swartz et al. |
| 5,725,522 A | 3/1998 | Sinofsky |
| 5,725,552 A | 3/1998 | Kotula et al. |
| 5,749,895 A | 5/1998 | Sawyer et al. |
| 5,757,772 A | 5/1998 | Thornberg et al. |
| 5,782,848 A | 7/1998 | Lennox |
| 5,782,860 A | 7/1998 | Epstein et al. |
| 5,810,810 A | 9/1998 | Tay et al. |
| 5,824,015 A | 10/1998 | Sawyer |
| 5,827,265 A | 10/1998 | Glinsky et al. |
| 5,827,268 A | 10/1998 | Laufer |
| 5,865,827 A | 2/1999 | Bullister |
| 5,868,702 A * | 2/1999 | Stevens et al. .......... 604/96.01 |
| 5,873,828 A | 2/1999 | Fujio et al. |
| 5,897,551 A | 4/1999 | Everett et al. |
| 5,919,188 A | 7/1999 | Shearon et al. |
| 5,919,191 A | 7/1999 | Lennox et al. |
| 5,919,200 A | 7/1999 | Stambaugh et al. |
| 5,925,078 A | 7/1999 | Anderson |
| 5,928,224 A | 7/1999 | Laufer |
| 5,928,266 A | 7/1999 | Kontos |
| 5,931,165 A | 8/1999 | Reich et al. |
| 5,944,738 A | 8/1999 | Amplatz et al. |
| 5,957,919 A | 9/1999 | Laufer |
| 5,964,782 A | 10/1999 | Lafontaine et al. |
| 5,972,026 A | 10/1999 | Laufer et al. |
| 5,984,909 A | 11/1999 | Lurie et al. |
| 5,989,284 A | 11/1999 | Laufer |
| 6,004,269 A | 12/1999 | Crowley et al. |
| 6,004,316 A | 12/1999 | Laufer |
| 6,010,516 A | 1/2000 | Hulka |
| 6,033,397 A | 3/2000 | Laufer et al. |
| 6,033,398 A | 3/2000 | Farley et al. |
| 6,036,687 A | 3/2000 | Laufer et al. |
| 6,048,333 A | 4/2000 | Lennox et al. |
| 6,063,081 A | 5/2000 | Mulier et al. |
| 6,063,085 A | 5/2000 | Tay et al. |
| 6,066,126 A | 5/2000 | Li et al. |
| 6,068,653 A | 5/2000 | LaFontaine |
| 6,071,277 A | 6/2000 | Farley et al. |
| 6,071,303 A | 6/2000 | Laufer |
| 6,083,219 A | 7/2000 | Laufer |
| 6,083,223 A | 7/2000 | Baker |
| 6,083,255 A | 7/2000 | Laufer et al. |
| 6,086,586 A | 7/2000 | Hooven |
| 6,087,552 A | 7/2000 | Gregory |
| 6,091,995 A | 7/2000 | Ingle et al. |
| 6,106,520 A | 8/2000 | Laufer et al. |
| 6,128,522 A | 10/2000 | Acker et al. |
| 6,132,429 A | 10/2000 | Baker |
| 6,135,997 A | 10/2000 | Laufer et al. |
| 6,139,527 A | 10/2000 | Laufer et al. |
| 6,149,660 A | 11/2000 | Laufer et al. |
| 6,152,139 A | 11/2000 | Laufer |
| 6,156,032 A | 12/2000 | Lennox |
| 6,165,206 A | 12/2000 | Tu |
| 6,168,594 B1 | 1/2001 | LaFontaine et al. |
| 6,200,315 B1 | 3/2001 | Gaiser et al. |
| 6,200,333 B1 | 3/2001 | Laufer |
| 6,206,907 B1 | 3/2001 | Marino et al. |
| 6,210,411 B1 | 4/2001 | Hofmann et al. |
| 6,211,335 B1 | 4/2001 | Owen et al. |
| 6,212,426 B1 | 4/2001 | Swanson |
| 6,221,068 B1 | 4/2001 | Fried et al. |
| 6,238,389 B1 | 5/2001 | Paddock et al. |
| 6,254,598 B1 | 7/2001 | Edwards et al. |
| 6,254,601 B1 | 7/2001 | Burbank et al. |
| 6,257,241 B1 | 7/2001 | Wampler |
| 6,258,087 B1 | 7/2001 | Edwards et al. |
| 6,273,886 B1 | 8/2001 | Edwards et al. |
| 6,273,907 B1 | 8/2001 | Laufer |
| 6,283,935 B1 | 9/2001 | Laufer et al. |
| 6,283,962 B1 | 9/2001 | Tu et al. |
| 6,283,988 B1 | 9/2001 | Laufer et al. |
| 6,283,989 B1 | 9/2001 | Laufer et al. |
| 6,290,674 B1 | 9/2001 | Roue et al. |
| 6,299,633 B1 | 10/2001 | Laufer |
| 6,302,898 B1 | 10/2001 | Edwards et al. |
| 6,323,037 B1 | 11/2001 | Lauto et al. |
| 6,325,798 B1 | 12/2001 | Edwards et al. |
| 6,338,731 B1 | 1/2002 | Laufer et al. |
| 6,352,534 B1 | 3/2002 | Paddock et al. |
| 6,355,030 B1 | 3/2002 | Aldrich et al. |
| 6,355,031 B1 | 3/2002 | Edwards et al. |
| 6,358,245 B1 | 3/2002 | Edwards et al. |
| 6,375,615 B1 | 4/2002 | Flaherty et al. |
| 6,379,368 B1 | 4/2002 | Corcoran et al. |
| 6,383,198 B1 | 5/2002 | Hamilton |
| 6,391,048 B1 | 5/2002 | Ginn et al. |
| 6,391,049 B1 | 5/2002 | McNally et al. |
| 6,398,779 B1 | 6/2002 | Buysse et al. |
| 6,398,782 B1 | 6/2002 | Pecor et al. |
| 6,398,797 B2 | 6/2002 | Bombard et al. |
| 6,401,719 B1 | 6/2002 | Farley et al. |
| 6,401,720 B1 | 6/2002 | Stevens et al. |
| 6,419,669 B1 | 7/2002 | Frazier et al. |
| 6,438,424 B1 | 8/2002 | Knowlton |
| 6,440,128 B1 | 8/2002 | Edwards et al. |
| 6,440,152 B1 | 8/2002 | Gainor et al. |
| 6,453,202 B1 | 9/2002 | Knowlton |

| | | | | | | |
|---|---|---|---|---|---|---|
| 6,461,314 B1 | 10/2002 | Pant et al. | | 2002/0107531 A1 | 8/2002 | Schreck et al. |
| 6,463,332 B1 | 10/2002 | Aldrich | | 2002/0128672 A1 | 9/2002 | Dinger et al. |
| 6,464,626 B1 | 10/2002 | Peterson | | 2002/0143324 A1 | 10/2002 | Edwards |
| 6,464,689 B1 | 10/2002 | Qin et al. | | 2002/0151871 A1 | 10/2002 | Gaiser et al. |
| 6,470,216 B1 | 10/2002 | Knowlton | | 2002/0169377 A1 | 11/2002 | Khairkhahan et al. |
| 6,482,203 B2 | 11/2002 | Paddock et al. | | 2002/0183787 A1 | 12/2002 | Wahr et al. |
| 6,488,673 B1 | 12/2002 | Laufer et al. | | 2002/0183789 A1 | 12/2002 | Neev |
| 6,494,879 B2 | 12/2002 | Lennox et al. | | 2002/0193787 A1 | 12/2002 | Qin et al. |
| 6,494,888 B1 | 12/2002 | Laufer et al. | | 2002/0193816 A1 | 12/2002 | Laufer et al. |
| 6,506,196 B1 | 1/2003 | Laufer | | 2003/0009194 A1 | 1/2003 | Saker et al. |
| 6,520,185 B1 | 2/2003 | Bommannan et al. | | 2003/0024538 A1 | 2/2003 | Edwards et al. |
| 6,524,326 B1 | 2/2003 | Zhu et al. | | 2003/0028188 A1 | 2/2003 | Paddock et al. |
| 6,526,302 B2 | 2/2003 | Hassett | | 2003/0028189 A1 | 2/2003 | Woloszko et al. |
| 6,529,778 B2 | 3/2003 | Prutchi | | 2003/0050632 A1 | 3/2003 | Fjield et al. |
| 6,547,776 B1 | 4/2003 | Gaiser et al. | | 2003/0069570 A1 | 4/2003 | Witzel et al. |
| 6,554,827 B2 | 4/2003 | Chandrasekaran et al. | | 2003/0078578 A1 | 4/2003 | Truckai et al. |
| 6,558,366 B1 | 5/2003 | Drasler et al. | | 2003/0092689 A1 | 5/2003 | Escandon et al. |
| 6,562,034 B2 | 5/2003 | Edwards et al. | | 2003/0093071 A1 | 5/2003 | Hauck et al. |
| 6,562,037 B2 | 5/2003 | Paton et al. | | 2003/0130730 A1 | 7/2003 | Cohn et al. |
| 6,562,052 B2 | 5/2003 | Nobles et al. | | 2003/0135206 A1 | 7/2003 | Edwards et al. |
| 6,565,557 B1 | 5/2003 | Sporri et al. | | 2003/0144652 A1 | 7/2003 | Baket et al. |
| 6,575,971 B2 | 6/2003 | Hauck et al. | | 2003/0144694 A1 | 7/2003 | Chanduszko et al. |
| 6,577,902 B1 | 6/2003 | Laufer et al. | | 2003/0158551 A1 | 8/2003 | Paton et al. |
| 6,583,117 B2 | 6/2003 | Owen et al. | | 2003/0178032 A1 | 9/2003 | Ingle et al. |
| 6,589,238 B2 | 7/2003 | Edwards et al. | | 2003/0191511 A1 | 10/2003 | Laufer et al. |
| 6,595,934 B1 | 7/2003 | Hissong et al. | | 2003/0191512 A1 | 10/2003 | Laufer et al. |
| 6,602,251 B2 | 8/2003 | Burbank et al. | | 2003/0195511 A1 | 10/2003 | Barry |
| 6,605,084 B2 | 8/2003 | Acker et al. | | 2003/0195593 A1 | 10/2003 | Ingle et al. |
| 6,606,513 B2 | 8/2003 | Lardo et al. | | 2003/0195604 A1 | 10/2003 | Ingle et al. |
| 6,613,047 B2 | 9/2003 | Edwards | | 2003/0208232 A1 | 11/2003 | Blaeser et al. |
| 6,629,534 B1 * | 10/2003 | St. Goar et al. ............ 128/898 | | 2004/0003819 A1 | 1/2004 | St. Goar et al. |
| 6,629,951 B2 | 10/2003 | Laufer et al. | | 2004/0039312 A1 | 2/2004 | Hillstead et al. |
| 6,635,052 B2 | 10/2003 | Loeb | | 2004/0059347 A1 | 3/2004 | Hamilton |
| 6,635,054 B2 | 10/2003 | Fjield et al. | | 2004/0122448 A1 * | 6/2004 | Levine ........................ 606/139 |
| 6,645,198 B1 | 11/2003 | Bommannan et al. | | 2004/0143294 A1 | 7/2004 | Corcoran et al. |
| 6,663,622 B1 | 12/2003 | Foley et al. | | 2004/0176752 A1 | 9/2004 | Alfano et al. |
| 6,663,639 B1 | 12/2003 | Laufer et al. | | 2004/0193147 A1 | 9/2004 | Malecki et al. |
| 6,669,655 B1 | 12/2003 | Acker et al. | | 2004/0230185 A1 | 11/2004 | Malecki et al. |
| 6,669,687 B1 | 12/2003 | Saadat | | 2004/0243122 A1 | 12/2004 | Auth et al. |
| 6,672,312 B2 | 1/2004 | Acker | | 2004/0267191 A1 | 12/2004 | Gifford et al. |
| 6,673,070 B2 | 1/2004 | Edwards et al. | | 2005/0021016 A1 | 1/2005 | Malecki et al. |
| 6,676,685 B2 | 1/2004 | Pedros et al. | | 2005/0033288 A1 | 2/2005 | Auth et al. |
| 6,699,243 B2 | 3/2004 | West et al. | | 2005/0034735 A1 | 2/2005 | Deem et al. |
| 6,702,835 B2 | 3/2004 | Ginn | | 2005/0055050 A1 | 3/2005 | Alfaro |
| 6,706,039 B2 | 3/2004 | Mulier et al. | | 2005/0065506 A1 | 3/2005 | Phan |
| 6,712,074 B2 | 3/2004 | Edwards et al. | | 2005/0070923 A1 | 3/2005 | McIntosh |
| 6,712,814 B2 | 3/2004 | Edwards et al. | | 2005/0080406 A1 | 4/2005 | Malecki et al. |
| 6,719,770 B2 | 4/2004 | Laufer et al. | | 2005/0131401 A1 | 6/2005 | Malecki et al. |
| 6,723,092 B2 | 4/2004 | Brown et al. | | 2005/0131460 A1 | 6/2005 | Gifford et al. |
| 6,728,565 B2 | 4/2004 | Wendlandt | | 2005/0192627 A1 | 9/2005 | Whisenant et al. |
| 6,733,495 B1 | 5/2004 | Bek et al. | | 2005/0192654 A1 | 9/2005 | Chanduszko et al. |
| 6,733,498 B2 | 5/2004 | Paton et al. | | 2005/0228283 A1 | 10/2005 | Gifford et al. |
| 6,775,575 B2 | 8/2004 | Bommannan et al. | | 2005/0267464 A1 | 12/2005 | Truckai et al. |
| 6,776,784 B2 | 8/2004 | Ginn | | 2005/0267523 A1 | 12/2005 | Devellian et al. |
| 6,782,565 B2 | 8/2004 | Hinton | | 2005/0267524 A1 | 12/2005 | Chanduszko |
| 6,783,523 B2 | 8/2004 | Qin et al. | | 2005/0267525 A1 | 12/2005 | Chanduszko |
| 6,790,207 B2 | 9/2004 | Utley et al. | | 2005/0267526 A1 | 12/2005 | Wahr et al. |
| 6,802,841 B2 | 10/2004 | Utley et al. | | 2006/0009800 A1 | 1/2006 | Christianson et al. |
| 6,821,285 B2 | 11/2004 | Laufer et al. | | 2006/0036282 A1 | 2/2006 | Wahr et al. |
| 6,827,713 B2 | 12/2004 | Bek et al. | | 2006/0036284 A1 | 2/2006 | Blaeser et al. |
| 6,836,688 B2 | 12/2004 | Ingle et al. | | 2006/0074410 A1 | 4/2006 | Malecki et al. |
| 6,852,108 B2 | 2/2005 | Barry et al. | | 2006/0079870 A1 * | 4/2006 | Barry ........................ 606/32 |
| 6,866,663 B2 | 3/2005 | Edwards et al. | | | | |
| 6,875,171 B2 | 4/2005 | Paolitto et al. | | FOREIGN PATENT DOCUMENTS | | |
| 6,887,238 B2 | 5/2005 | Jahns et al. | | | | |
| 6,939,348 B2 | 9/2005 | Malecki et al. | | WO | WO-97/32532 | 9/1997 |
| 2001/0051800 A1 | 12/2001 | Eugeny et al. | | WO | WO-98/38936 | 9/1998 |
| 2002/0042564 A1 | 4/2002 | Cooper et al. | | WO | WO-99/18826 | 4/1999 |
| 2002/0068932 A1 | 6/2002 | Edwards et al. | | WO | WO-99/18862 | 4/1999 |
| 2002/0082621 A1 | 6/2002 | Schurr et al. | | WO | WO-99/18864 | 4/1999 |
| 2002/0091379 A1 | 7/2002 | Danek et al. | | WO | WO-99/18870 | 4/1999 |
| 2002/0095164 A1 | 7/2002 | Andreas et al. | | WO | WO-99/18871 | 4/1999 |
| 2002/0107512 A1 | 8/2002 | Edwards | | WO | WO-99/32040 | 7/1999 |

| | | |
|---|---|---|
| WO | WO-99/34741 | 7/1999 |
| WO | WO-99/42044 | 8/1999 |
| WO | WO-99/42045 | 8/1999 |
| WO | WO-00/18307 | 4/2000 |
| WO | WO-00/18308 | 4/2000 |
| WO | WO-00/51510 | 9/2000 |
| WO | WO-00/57495 | 9/2000 |
| WO | WO-00/64387 | 11/2000 |
| WO | WO-00/66006 | 11/2000 |
| WO | WO-00/66015 | 11/2000 |
| WO | WO-00/66018 | 11/2000 |
| WO | WO-00/66019 | 11/2000 |
| WO | WO-00/66021 | 11/2000 |
| WO | WO-00/66052 | 11/2000 |
| WO | WO-01/10314 | 2/2001 |
| WO | WO-01/17450 | 3/2001 |
| WO | WO-02/24092 | 3/2002 |
| WO | WO-02/058780 | 8/2002 |
| WO | WO-02/060523 A2 | 8/2002 |
| WO | WO-02/060523 A3 | 8/2002 |
| WO | WO-02/067798 | 9/2002 |
| WO | WO-2004/043266 A2 | 5/2004 |
| WO | WO-2004/069055 A2 | 8/2004 |

OTHER PUBLICATIONS

U.S. Appl. No. 11/243,324, Barry.
U.S. Appl. No. 60/474,055, Auth et al.
U.S. Appl. No. 60/477,760, Auth et al.
Caceci, Dr. Thomas, Text on Skeletal Muscle and Collagen Remodeling (10 pages).
Chapter 6: Percutaneous Closure of Heart Defects, 2002, Health Research International (3 Pages).
Chatterjee, T. et al., "Nonsurgical Closure of Secundum Atrial Septal Defect and Patent Foremen Ovale," J Clin Basic Cardiol 4:35, 2001, Bern, Switzerland (4 Pgs.).
ConMed Corporation, "Suction Instruments & Tubing," (6 Pgs.).
Gifford, H. et al., "Methods and Apparatus for Treatment of patent Foramen Ovale," http://www.freshpatents.com/Methods-and-apparatus-for-treatment-of-patent-foramen-ovale-dt20050616ptan20050131460.php, Internet Pages 1-2, Jul. 18, 2005.
Harper, R. et al., "Closure of Secundum Atrial Septal Defects With the Amplatzer Septal Occluder Device: Techniques and Problems," Catheterization and Cardiovascular Interventions, 2002, pp. 508-524, vol. 57, Wiley-Liss, Inc.
International Search Report for PCT/US2004/040786; Feb. 2004; Applicant: CoAptus Medical Corporation (8 Pages).
Johnston, J. H. et al., "Experimental Comparison of Endoscopic Yttrium-Aluminum-Garnet Laser, Electrosurgery, and Heater Probe for Canine Gut Arterial Coagulation: Importance of Compression and Avoidance of Erosion," Gastroenterology, 1987, pp. 1101-1108, vol. 92, No. 5, American Gastroenterological Association.
Karttunen, V. et al., "Ear Oximetry: A Noninvasive Method for Detection of Patent Foramen Ovale, A Study Comparing Dye Dilution Method and Oximetry With Contrast Transesophageal Echocardiography," Stroke, Feb. 2001, vol. 32, pp. 448-453, American Heart Association, Inc.
Kerut, E. et al., "Patent Foramen Ovale: A Review of Associated Conditions and the Impact of Physiological Size,"Journal of the American College of Cardiology, Sep. 2001, pp. 613-623, vol. 38, No. 3, Elsevier Science, Inc.
Knebel, F., "Percutaneous Closure of Interatrial Communications in Adults-Prospective Embolism Prevention Study With Two and Three Dimensional Echocardiography," Cardiovascular Ultrasound, May 19, 2004, 2:5, (10 Pages.).
Kramer, P., "The Hidden Connection," Endovascular Today, May 2004, pp. 47-52.
Lipton, R. et al., "Epidemiology and Economic Impact of Migraine," www.medscape.com/viewarticle/429665 <http://www.medscape.com/viewarticle/429665>.
Curr Med Res Opin, 2001, 17(1s):s4-s12, Medscape.

Madison Skin & Laser Center, Thermalift™ Pre-Treatment Instructions & Thermalift™ Discharge Instructions. (2 Pages).
Malecki, W. et al., "Energy Based Devices and Methods for Treatment of Anatomic Tissue Defects," http://www.freshpatents.com/Energy-based-devices-and-methods-for-treatment-of-anatomic-tissue-defects-dt20050616ptan20050131401.php, Internet pp. 1-2, Jul. 18, 2005.
Malis, L., "Electrosurgery," J. Neurosurg., Nov. 1996, pp. 970-975, vol. 85.
Marshall, A. et al., "Structural and Compliant Anatomy of the Patent Foramen Ovale in Patients Undergoing Transcatheter Closure," American Heart Journal, Aug. 2000, pp. 303-307, vol. 140, No. 2, © Mosby, Inc.
Mayo Clinic, "Patent foremen Ovale: Paradoxical Embolism and Paradoxical Data," Mayo Clinic Proceedings, Jan. 2004, pp. 15-20, vol. 79, No. 1, Mayo Foundation for Medical Education and Research.
McClurken, M. et al., "Collagen Shrinkage and Vessel Sealing," TissueLink Medical, Inc., Technical Brief #300, TissueLink, Dover, NH.
McClurken, M. et al., "Thermal Effect of Tissue Link™ Technology on liver," TissueLink Medical, Inc., Technical Brief #301, TissueLink, Dover, NH.
McMahon, C.J. et al., "Use of the Transseptal Puncture in Transcatherer Closure of Long Tunnel-Type Patent Foramen Ovale," Heart, Aug. 2002, 88:e3, (2 Pages).
Meier, B. et al., "Contemporary Management of Patent Foramen Ovale," Circulation, Jan. 7/14, 2003, pp. 5-9, American Heart Association.
Meier, B., "Patent Foramen Ovale-Bearty Spot or Health Threat," CardiologyRounds, pp. 1-8, vol. 5, Issue 10, Dec. 2001, Brigham and Women's Hospital, Boston, Massachuetts.
Nkomo, V., et al. "Patent Foramen Ovale Transcatheter Closure Device Thromboisis," Mayo Clin Proc., Oct. 2001, pp. 1057-1061, vol. 76, © Mayo Foundation for Medical Education and Research.
NMT Medical, Inc. Brochure, "Cardioseal Septal Occlusion Systems," ML-0038.00, www.nmtmedical.com <http://www.nmtmedical.com>, Boston, MA (2 Pages).
NMT Medical, Inc. Brochure, "PFO Closure: Outcomes and Device Design Frequesently Asked Questions," ML-0116.00, pp. 1-4, www.nmtmedical.com <http://www.nmtmedical.com>, Boston, MA.
Overell, J.R. et al., "Interatrial Septal Abnormabilities and Stroke," Neurology, Oct. (2 of 2), 2000, vol. 55, pp. 1172-1179, © AAN Enterprises.
Patent Foramen Ovale [PFO], (1 Page).
Rosenbaum, M. et al., "An Exploratory Investigation of the Morphology and Biochemistry of Cellulite," Journal of the American Society of Plastic Surgeons, Jun. 1993, pp. 1934-1939, vol. 101, Issue 7, Lippincott,Willams & Wilkins. (*Abstract Provided-2 Pages*).
Ruiz, C. et al., "The Puncture Technique: A New Method for Transcatheter Closure of Patent Foramen Ovale," Catheterization and Cardiovascular Interventions, 2001, pp. 369-372, vol. 53, Wiley-Liss, Inc.
Schuchlenz, H. et al., "Transesophageal Echocardiography For Quantifying Size of Patent Foramen Ovale in patients With Cryptogenic Cerebrovascular Events, " Stroke, Jan. 2003, p. 293-296, American Heart Association.
Schwerzmann, M. et al., "Percutaneous Closure of Patent Foramen Ovale Reduces the Frequency of Migraine Attacks," Neurology, Apr. (2 of 2), 2004, pp. 1399-1401, vol. 62, AAN Enterprises, Inc.
Shepard, S., "TissueLink's Hemostasis Device Stirs Interest of Local Surgeons," TissueLink, Nov. 7, 2003, Print Edition (3 Pages).
Silverglide, Surgical Technologies, inc., "What Makes SILVERGlide Non-Stick Bipolar Forceps Different." (1 Page).
Stuart, M., "Stroke Prevention: The Newest Frontier in Interventional Cardiology," Interventional Cardiology, Oct. 2003, p. 23-28, Windhover Information Inc.

Szil-Torok, T. et al., "Transseptal Left Heart Catheterisation Guided by Intracardiac Echocardiography," Heart, 2001, 86:e11, Dept. of Cardiology, Rotterdam, The Netherlands, (5 Pages).

The Thermage Procedure Brochure. (2 Pages).

Walsh, K.P. et al., "Transcatheter closure of patent foramen ovale Using the Amplatzer Septal Occluder to Prevent Recurrence of Neurological Decompression Illness in Divers," Heart 1999, pp. 257-261, vol. 81.

Wright, N. et al., "Denaturation of Collagen via Heating: An Irreversible Rate Process," Annual Review of Biomedical Engineering, 2002, pp. 109-128, vol. 4.

U.S. Appl. No. 60/458,854, Gifford.

U.S. Appl. No. 60/478,035, Gifford et al.

U.S. Appl. No. 60/490,082, Deem et al.

* cited by examiner

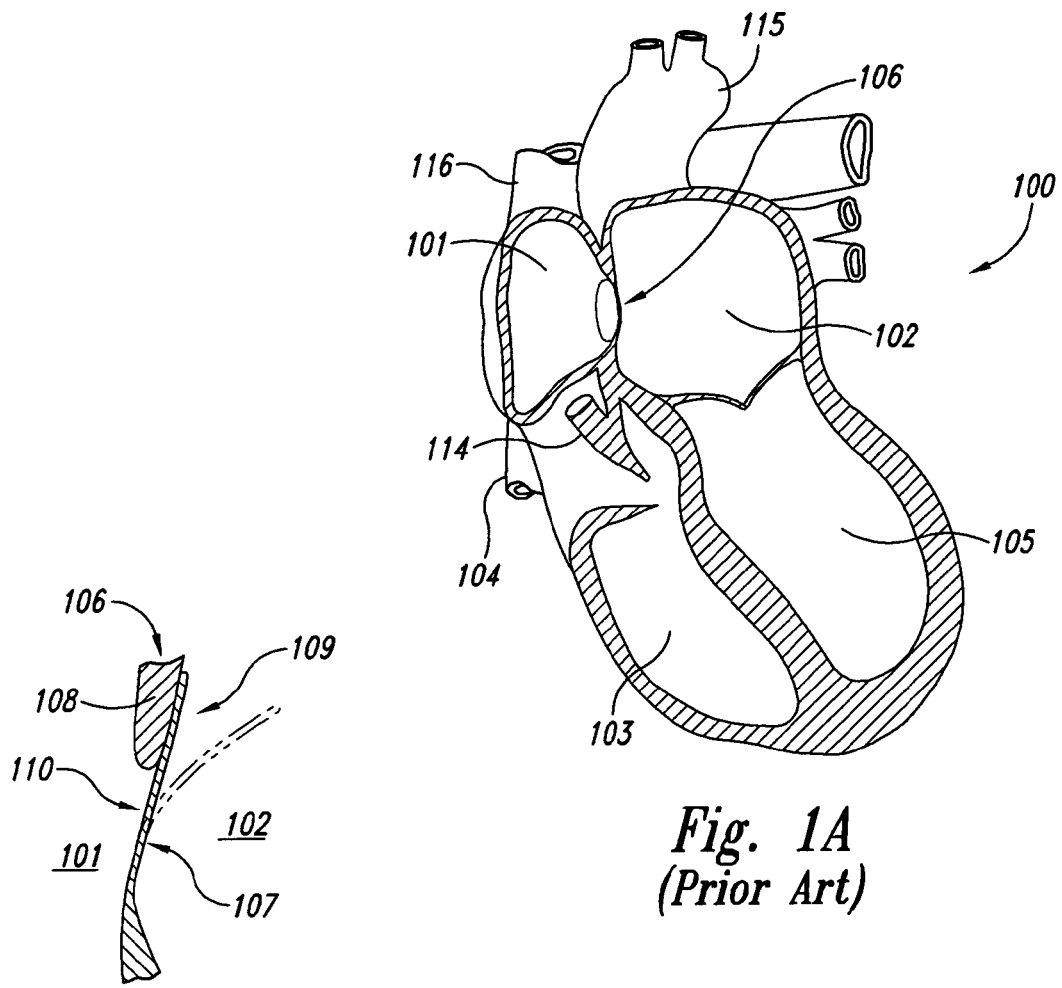
Fig. 1A
(Prior Art)
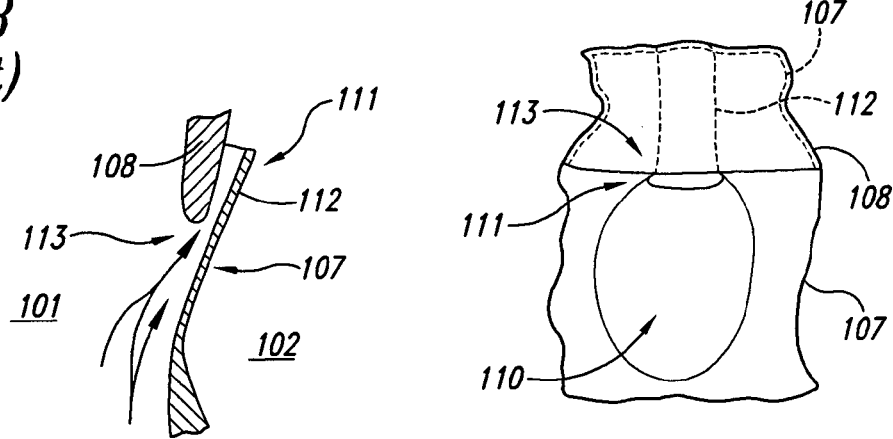
Fig. 1B
(Prior Art)
Fig. 1C
(Prior Art)
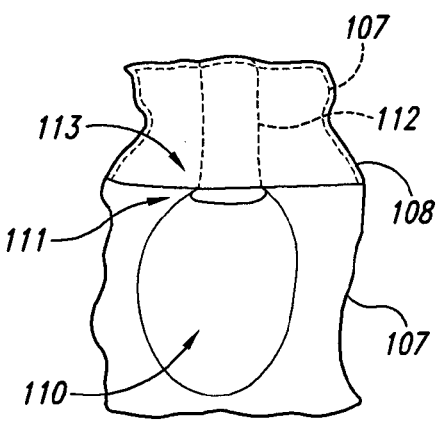
Fig. 1D
(Prior Art)

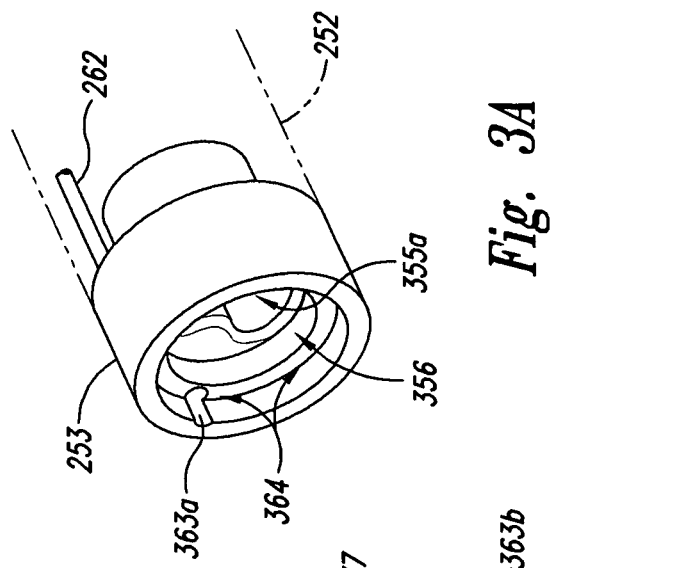
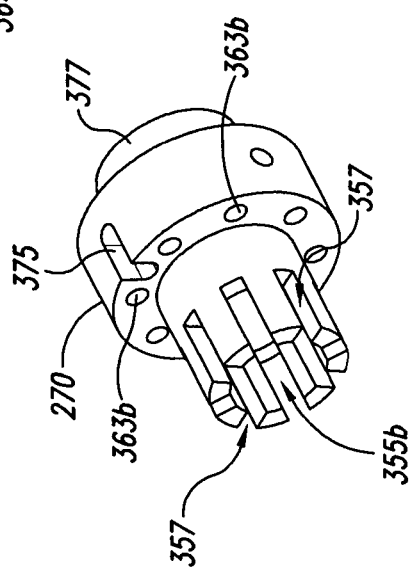
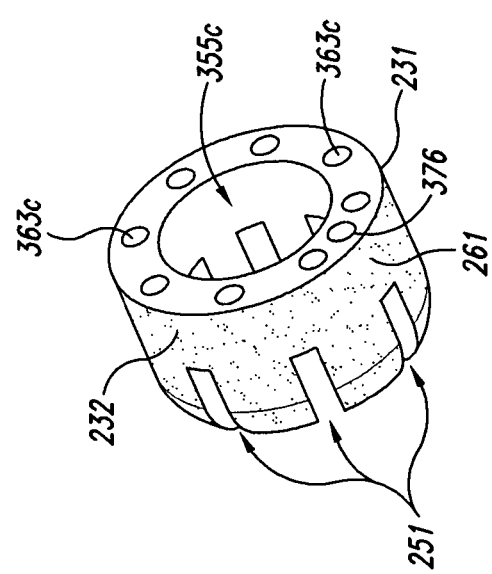
Fig. 3A
Fig. 3B
Fig. 3C

SYSTEMS AND METHODS FOR SECURING CARDIOVASCULAR TISSUE

CROSS REFERENCES TO OTHER RELATED APPLICATIONS

The present application is a continuation-in-part (CIP) of U.S. patent application Ser. No. 10/754,790 filed Jan. 8, 2004 which claims the benefit of Provisional Application Ser. No. 60/447,760 filed Feb. 13, 2003 and Provisional Application Ser. No. 60/474,055 filed May 28, 2003; and of U.S. patent application Ser. No. 10/856,475 filed May 28, 2004 which claims the benefit of Provisional Application Ser. No. 60/474,055 filed May 28, 2003. The present application claims priority under 35 USC 119(e) to Provisional Application Ser. No. 60/616,252 filed Oct. 5, 2004 and Provisional Application Ser. No. 60/617,247 filed Oct. 7, 2004.

TECHNICAL FIELD

The present invention is directed generally to systems and methods for securing cardiovascular tissue, including systems and methods for applying a vacuum from within a patent foramen ovale (PFO) to draw cardiac tissue together and close the PFO.

BACKGROUND

The human heart is a complex organ that requires reliable, fluid-tight seals to prevent de-oxygenated blood and other constituents received from the body's tissues from mixing with re-oxygenated blood delivered to the body's tissues. FIG. 1A illustrates a human heart 100 having a right atrium 101, which receives the de-oxygenated blood from the superior vena cava 116 and the inferior vena cava 104. The de-oxygenated blood passes to the right ventricle 103, which pumps the de-oxygenated blood to the lungs via the pulmonary artery 114. Re-oxygenated blood returns from the lungs to the left atrium 102 and is pumped into the left ventricle 105. From the left ventricle 105, the re-oxygenated blood is pumped throughout the body via the aorta 115.

The right atrium 101 and the left atrium 102 are separated by an interatrial septum 106. As shown in FIG. 1B, the interatrial septum 106 includes a primum 107 and a secundum 108. Prior to birth, the primum 107 and the secundum 108 are separated to form an opening (the foramen ovale 109) that allows blood to flow from the right atrium 101 to the left atrium 102 while the fetus receives oxygenated blood from the mother. After birth, the primum 107 normally seals against the secundum 108 and forms an oval-shaped depression, i.e., a fossa ovalis 110.

In some infants, the primum 107 never completely seals with the secundum 108, as shown in cross-sectional view in FIG. 1C and in a left side view in FIG. 1D. In these instances, a patency 111 often having the shape of a tunnel 112 forms between the primum 107 and the secundum 108. This patency is typically referred to as a patent foramen ovale or PFO 113. In most circumstances, the PFO 113 will remain functionally closed and blood will not tend to flow through the PFO 113, due to the higher pressures in the left atrium 102 that secure the primum 107 against the secundum 108. Nevertheless, during physical exertion or other instances when pressures are greater in the right atrium 101 than in the left atrium 102, blood can inappropriately pass directly from the right atrium 101 to the left atrium 102 and can carry with it clots or gas bubbles. Such constituents in the atrial system can pose serious health risks including hemodynamic problems, cryptogenic strokes, venous-to-atrial gas embolism, migraines, and in some cases even death.

Traditionally, open chest surgery was required to suture or ligate a PFO 113. However, these procedures carry high attendant risks, such as postoperative infection, long patient recovery, and significant patient discomfort and trauma. Accordingly, less invasive techniques have been developed. Most such techniques include using a transcatheter implantation of various mechanical devices to close the PFO 113. Such devices include the Cardia® PFO Closure Device, Amplatzer® PFO Occluder, and CardioSEAL® Septal Occlusion Device. One potential drawback with these devices is that they may not be well suited for the long, tunnel-like shape of the PFO 113. As a result, the implanted mechanical devices may become deformed or distorted and in some cases may fail, migrate, or even dislodge. Furthermore, these devices can irritate the cardiac tissue at or near the implantation site, which in turn can potentially cause thromboembolic events, palpitations, and arrhythmias. Other reported complications include weakening, erosion, and tearing of the cardiac tissues around the implanted devices.

Another potential drawback with the implanted mechanical devices described above is that, in order to be completely effective, the tissue around the devices must endothelize once the devices are implanted. The endothelization process can be gradual and can accordingly take several months or more to occur. Accordingly, the foregoing techniques do not immediately solve the problems caused by the PFO 113.

Still another drawback associated with the foregoing techniques is that they can be technically complicated and cumbersome. Accordingly, the techniques may require multiple attempts before the mechanical device is appropriately positioned and implanted. As a result, implanting these devices may require long procedure times during which the patient must be kept under conscious sedation, which can pose further risks to the patient.

BRIEF DESCRIPTION OF THE DRAWINGS

FIGS. 1A-1D illustrate a human heart having a patent foramen ovale (PFO) in accordance with the prior art.

FIGS. 3A-3C illustrate details of an embodiment of the catheter shown in FIGS. 2A-2D.

DETAILED DESCRIPTION

A. Introduction

Figure 2A:
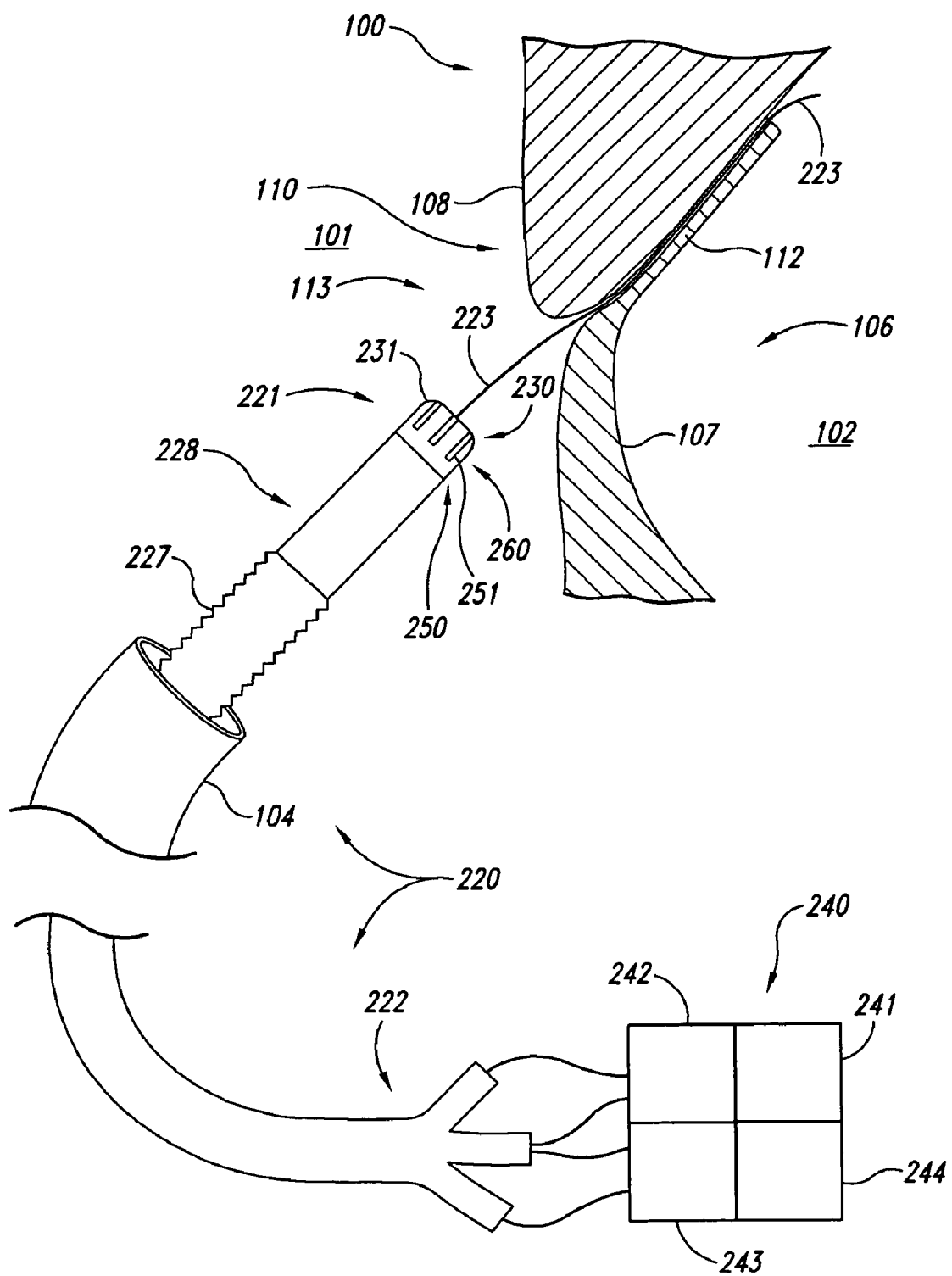
FIGS. 2A-2D illustrate a catheter configured in accordance with an embodiment of the invention, and a method for using the catheter to draw cardiac tissue together and seal the cardiac tissue.

The present invention is directed generally to methods and devices for drawing portions of cardiovascular tissue together and, in many cases, sealing the portions to each other. For example, devices in accordance with particular embodiments of the invention can be placed within the tunnel of a patent foramen ovale (PFO), formed between the primum and secundum. A vacuum drawn from within the tunnel can be used to draw portions of the tunnel toward each other. An energy transmitter (e.g., an electrode) can be used to fuse the portions of tissue together to close the patency. Well-known structures, systems, and methods often associated with these systems have not been shown or described in detail to avoid unnecessarily obscuring the description of the various embodiments of the invention. Details of related embodiments are provided in co-pending U.S. application Ser. No. 10/754,790, filed Jan. 8, 2004, and Ser. No. 10/856,475 entitled "Transseptal Left Atrial Access and Septal Closure," filed May 28, 2004, both of which are incorporated herein by reference. Those of ordinary skill in the relevant art will understand that additional embodiments of the invention may be practiced without several of the details described below.

A method in accordance with one aspect of the invention includes inserting a portion of a catheter into an opening between a first portion of cardiovascular tissue (e.g., the primum) and a second portion of cardiovascular tissue (e.g., the secundum). The method can further include drawing the first and second portions of the cardiovascular tissue into contact with each other by drawing a vacuum in a region between the first and second portions of the cardiovascular tissue via the catheter while the catheter is positioned between the first and second portions. The vacuum can accordingly be used to hold the first and second portions of tissue relative to each other, and/or to hold the catheter relative to the first and second portions of the tissue. The method can still further include securing the first and second portions of the tissue to each other, for example, by applying an energy to the first and second portions of the cardiovascular tissue. In a particular aspect of this invention, the energy can include RF energy supplied by one or more electrodes carried at the distal end of the catheter.

When the energy includes electrical RF energy, it can be delivered to the cardiovascular tissue in a number of manners, including monopolar delivery, bipolar delivery, multi-polar delivery, combinations of bipolar and multipolar delivery, including simultaneous delivery of each with multiple waveforms, some of which may be arranged in controlled phase with respect to each other, for example 90° phase shift or phase quadrature. The electrode(s) used to deliver the electrical current can be fitted with peripherally located vacuum ports, for example, to bring the portions of cardiovascular tissue into intimate contact with each other and with the electrode(s). In particular embodiments, additional techniques are used to prevent or at least restrict the cardiovascular tissue from fusing or otherwise adhering to the electrode(s). Such techniques can include placing a nonstick material on the electrode(s) and/or pumping a liquid (e.g., an electrically conductive liquid that promotes heat production at the interface of the first and second tissue portions) through a porous portion of the electrode(s).

A device for treating cardiovascular tissue in accordance with another aspect of the invention can include a catheter having a proximal end and a distal end. An energy transmitter can be positioned toward the distal end of the catheter and can be configured to be received in an opening between the first portion of the cardiovascular tissue and the second portion of the cardiovascular tissue. The energy transmitter can be coupleable to an energy source to fuse the first and second portions of the cardiovascular tissue while the energy transmitter is positioned in the opening. A vacuum channel can be positioned in the catheter and can have at least one port proximate to the distal end of the catheter and configured to be received in the opening between the first and second tissue portions. The vacuum channel can be coupleable to a vacuum source to draw the first and second portions of cardiac tissue together.

In further particular aspects of the invention, the energy transmitter can include at least one electrode coupleable to a source of electrical power, and the device can further include a return electrode that is coupleable to a patient at a location superior to the at least one electrode. For example, the return electrode can be coupleable to a patient at a location superior to the patient's heart so as to direct electrical field lines superiorly from the catheter to the tissue portions that are to be fused. In still further embodiments, the catheter can include an inflatable chamber positioned proximate to its distal end. The inflatable chamber can have an inflated dimension that is larger than a corresponding dimension of the opening between the first and second portions of the cardiovascular tissue. Accordingly, the inflatable chamber can be used to locate the distal end of the catheter within the space between the first and second portions of the cardiac tissue, and/or to seal the catheter against the first and second portions.

B. Systems and Methods for Treating Cardiac Tissue

FIGS. 2A-2D illustrate a catheter 220 and methods for using the catheter to treat cardiovascular tissue, in accordance with several embodiments of the invention. These Figures, as well as FIGS. 3A-5 and the associated discussion, illustrate implementations of representative devices and methods in the context of cardiac tissues. In other embodiments, these devices and methods may be used in conjunction with other tissues, including other cardiovascular tissues (e.g., veins and arteries). Beginning with FIG. 2A, the catheter 220 can include a proximal end 222 coupleable to a control unit 240, and a distal end 221 having a working portion 228 configured to be placed in a patient's heart 100. A flexible portion 227 between the distal end 221 and the proximal end 222 can allow the catheter 220 to absorb stresses without disturbing the working portion 228. The distal end 221 can be inserted into the patient's heart 100 via the inferior vena cava 104 or another blood vessel. The catheter 220 can include a vacuum system 250 having vacuum ports 251 that are used to evacuate fluids (and/or solids, e.g., blood clots) in the regions surrounding the distal end 221. The force of the applied vacuum can accordingly draw portions of cardiac tissue toward each other and toward the catheter 220. The catheter 220 can also include an energy transmitter 230 (e.g., an electrode 231) that directs energy to the cardiac tissue portions to fuse the tissue portions together. A fluid supply system 260 can provide fluid to the working portion 228 to prevent the cardiac tissue from fusing to the electrode 231 or other portions of the energy transmitter 230 and/or to increase the penetration of the electrical field provided by the electrode 231.

The control unit 240 can control and/or monitor the operation of the energy transmitter 230, the vacuum system 250, and the fluid supply system 260. Accordingly, the control unit 240 can include an energy transmitter control/monitor 241, a vacuum control/monitor 242, and a fluid supply control/monitor 243. The control unit 240 can also include other controls 244 for controlling other systems or subsystems that form portions of, or are used in conjunction with, the catheter 220. Such subsystems can include but are not limited to, temperature and/or impedance detectors that determine the temperature and/or impedance of the cardiac tissue and can be used to prevent the energy transmitter 230 from supplying excessive energy to the cardiac tissue. The subsystems can also include current sensors to detect the current level of electrical signals applied to the tissue, voltage sensors to detect the voltage of the electrical signals, and/or vision devices that aid the surgeon or other practitioner in guiding the catheter 220. The control unit 240 can include programmable, computer-readable media, along with input devices that allow the practitioner to select control functions, and output devices (e.g., display screens) that present information corresponding to the operation of the catheter 220.

In a particular embodiment shown in FIG. 2A, the catheter 220 is inserted into the right atrium 101 to seal a PFO 113 that exists in the interatrial septum 106 between the right atrium 101 and the left atrium 102. Accordingly, the practitioner can first insert a guide wire 223 into the right atrium 101 and through the tunnel portion 112 of the PFO 113, using one or more suitable guide techniques. For example, the guide wire 223 can be moved inferiorly along the interatrial septum 106 until it "pops" into the depression formed by the fossa ovalis 110. This motion can be detected by the practitioner at the proximal end 222 of the catheter 220. The tunnel 112 will typically be at least partially collapsed on itself prior to the insertion of the catheter 220, so the practitioner will likely probe the fossa ovalis 110 to locate the tunnel entrance, and then pry the tunnel 112 open. Suitable imaging/optical techniques (e.g., fluoroscopic techniques, intracardiac echo or ICE techniques and/or transesophageal electrocardiography or TEE) can be used in addition to or in lieu of the foregoing technique to thread the guide wire 223 through the tunnel 112. Corresponding imaging/optical devices can be carried by the catheter 220.

Figure 2B:
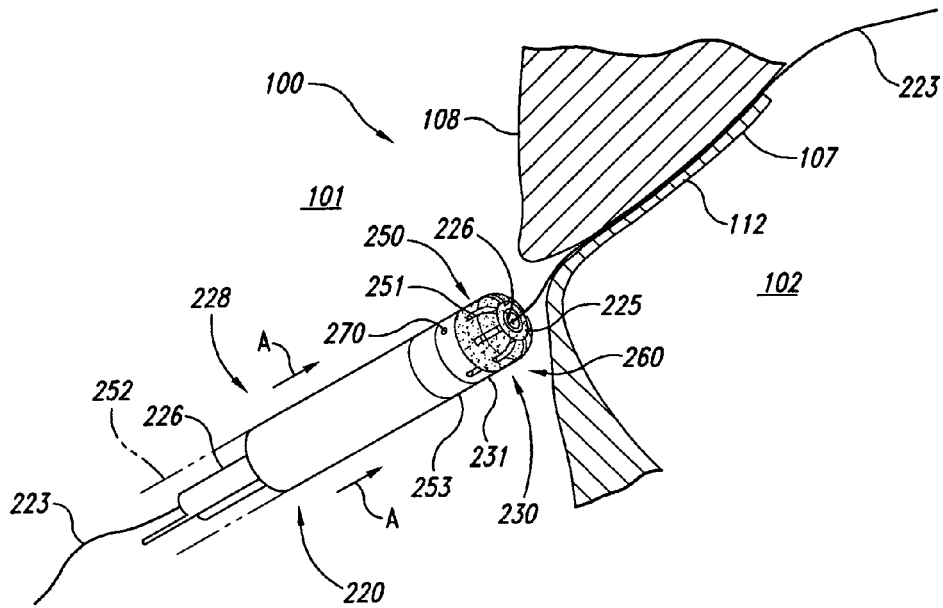

Referring next to FIG. 2B, the working portion 228 of the catheter 220 can be advanced along the guide wire 223, as indicated by arrows A. The working portion 228 can include a fluid manifold 253 for handling fluids supplied to and/or withdrawn from the heart 100, and an electrode holder 270 that supports the electrode 231. A guide wire holder 225 at the tip of the electrode 231 surrounds a guide wire conduit 226 through which the guide wire 223 passes, so as to keep the catheter 220 aligned along the guide wire 223.

As the catheter 220 is moved toward the tunnel 112, the practitioner can activate the vacuum system 250. The vacuum system 250 can include an internal vacuum passage coupled to vacuum ports 251 formed in the exterior surface of the electrode 231. Accordingly, the vacuum system 250 can draw in fluid from the region immediately surrounding the distal end 221 of the catheter 220 through the vacuum ports 251. The fluid drawn through the vacuum ports 251 can be evacuated from the patient's body via a vacuum line 252 that surrounds the guide wire conduit 226.

The catheter 220 can have a diameter of from about 3 to about 5 millimeters (9-15 French) and in one embodiment, a diameter of about 4 millimeters. This size allows the catheter 220 to fit into most (clinically symptomatic) tunnels 112. The practitioner can select smaller catheters 220 for very small tunnels 112. For larger tunnels 112, the practitioner can use larger catheters 220, or multiple catheters 220 in parallel, or multiple, sequential fusion operations with a single catheter 220. As described below, using a catheter having a size on the same order as the size of the tunnel 112 (e.g., a catheter occupying at least 40% of the tunnel 112) can allow the catheter 220 to draw the primum 107 and the secundum 108 into close contact with each other when the catheter 220 is inserted into the PFO tunnel 112.

Figure 2C:
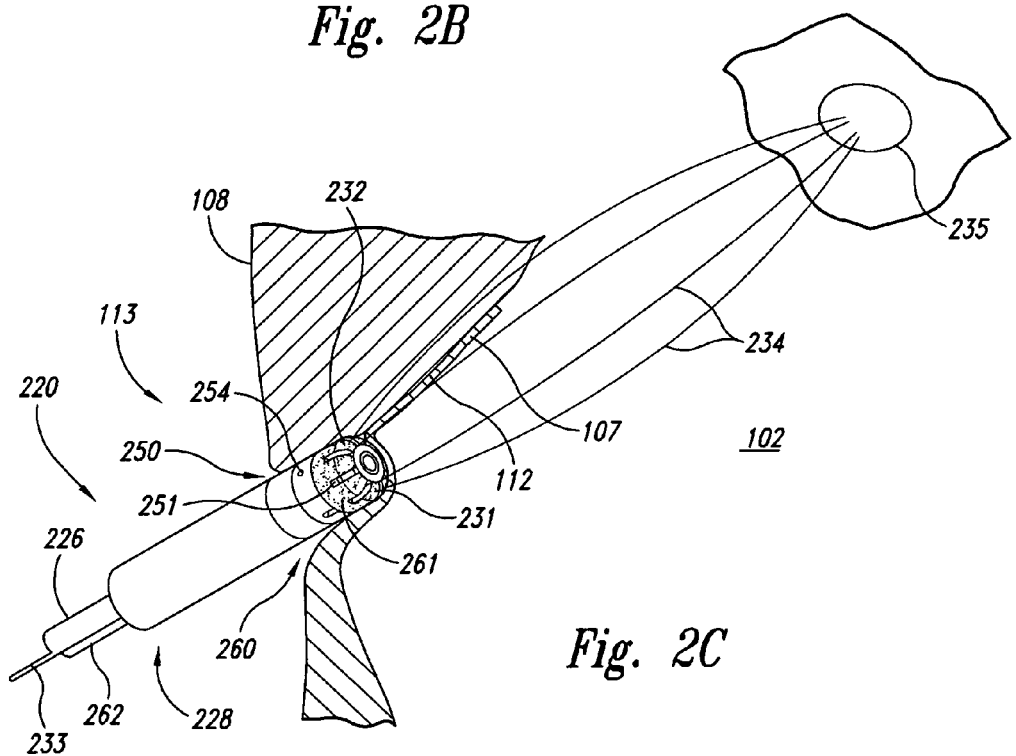

FIG. 2C illustrates the catheter 220 after the working portion 228 has been inserted part way into the tunnel 112. As the catheter 220 advances into the tunnel 112, an outer periphery 232 of the electrode 231 begins to contact both the primum 107 and the secundum 108. At the same time, the vacuum system 250 continues to draw liquid through the vacuum ports 251 and also through a locating port 254. Accordingly, the cardiac tissue will begin to seal or clamp against the vacuum ports 251. The practitioner can continue to insert the catheter 220 until the locating port 254 is covered by cardiac tissue, optionally by temporarily reducing the vacuum pressure to allow for easier movement of the catheter 220. At this point, the catheter 220 has been inserted into the tunnel 112 by a target distance, preselected to provide good sealing performance. The target distance can be from about 1 to about 15 millimeters for typical PFOs 113. With the catheter at this position, the tunnel 112 is completely collapsed on itself, causing the primum 107 to coarct with (e.g., clamp against and/or conform closely with) the secundum 108. The primum 107 can also stretch and coarct with the periphery 232 of the electrode 231. Accordingly, the catheter 220 is secured in a position relative to the PFO 113, and the guide wire 223 (FIG. 2B) can be withdrawn from the tunnel 112. The vacuum provided by the catheter 220 can optionally also be used to remove blood clots from the PFO 113, if desired.

The level of vacuum applied by the catheter 220 can be varied during the insertion process and/or other processes. For example, the practitioner can set the vacuum level to a relatively low differential pressure to partially secure the cardiac tissue while the guide wire 223 (FIG. 2B) is in the tunnel 112. The practitioner can increase the differential pressure after the guide wire 223 is removed to more completely secure the catheter 220.

During the foregoing insertion process, the catheter 220 can have any rotational position relative to the guide wire 223 (FIG. 2B) without affecting performance. This simplifies the insertion task because the practitioner need not track or adjust the rotational orientation of the catheter 220. During the foregoing insertion process, the practitioner can also receive positive feedback indicating that the catheter 220 is secured within the tunnel 112. For example, the practitioner can observe a decrease in the rate at which fluid is withdrawn from the patient (via the vacuum system 250) when the catheter 220 seals the tunnel 112. In particular examples, the practitioner can observe a fluid drip, or (for higher flowrates) a flowmeter, or another monitoring device. The practitioner can also observe an increase in the differential pressure pulled by the vacuum system 250 when the tunnel 112 collapses on itself and against the vacuum ports 251. For example, the practitioner can observe a vacuum gauge.

Prior to providing electrical power to the electrode 231, the practitioner can activate the fluid supply system 260. The fluid supply system 260 can pump fluid through a fluid supply line 262 and through pores 261 located at the working portion 228 of the catheter 220 (e.g., in a peripheral surface 232 of the electrode 231). The fluid can be selected to be electrically conductive so as not to interfere with the transmission of electrical signals to the cardiac tissues by the electrode 231. For example, the fluid can be selected to include a saline solution having normal concentration (e.g., 0.9%) or higher concentrations (e.g., 3%-4%). The flow rate of the fluid can be selected to form a thin film of fluid between the electrode 231 and the adjacent cardiac tissue. The flow rate can be low enough to form a thin fluid film that does not interfere with the ability of the vacuum system 250 to hold the primum 107 and the secundum 108 together. In this manner, the vacuum system 250 and the fluid supply system 260 can be operated in conjunction with each other to: (a) secure the electrode 231 relative to the PFO 113, (b) secure the primum 107 and the secundum 108 against each other while they are fused together, and (c) prevent or at least restrict fusion between the cardiac tissue and the electrode 231. Representative flow rates and pressures are described below with reference to FIG. 3B.

In a particular embodiment, the fluid supply system 260 can be activated for about 5 seconds before activating the electrode 231. In other embodiments, this time period can have different values. In any of these embodiments, the fluid can perfuse the adjacent cardiac tissue with electrically conducting ions to increase the efficiency with which electrical energy is transmitted into and/or through the tissue. For purposes of illustration, a single supply line 262 is shown in FIG. 2C. In other embodiments, the fluid system 260 can supply multiple fluids independently through multiple supply lines. The multiple fluids can have different properties, and can be electrically isolated from each other via the multiple supply lines.

The configuration shown in FIG. 2C employs a monopolar electrode 231 coupled to an electrical lead 233. Accordingly, the practitioner places a return electrode 235 remote from the treatment site to provide a conductive return path for electrical current provided by the electrode 231. Most conventional return electrodes are placed against the patient's buttocks and have a large surface area so as to reduce the likelihood for burning. Unlike these conventional return electrodes, the return electrode 235 can be relatively small (e.g., about four inches in diameter), and can be placed superior to the PFO 113 (e.g., superior to the patient's heart 100). When a current is applied to the electrode 231, the resulting electrical field forms flux lines 234 extending generally between the electrode 231 and the return electrode 235. For purposes of illustration, only those flux lines 234 extending more or less directly between the electrode 231 and the return electrode 235 are shown in FIG. 2C. Accordingly, the flux lines 234 can be aligned with the interface between the primum 107 and the secundum 108. The electrical current can therefore fuse the primum 107 to the secundum 108 along at least a portion of the length of the tunnel 112. The current path in the embodiment extends into a bloody field of the left atrium 102 after passing through the primum 107. For example, about 10% of the electrical current can pass through the left atrial blood. In other embodiments, the return electrode 235 can have other locations relative to the heart 100, e.g., offset laterally from the heart 100.

The electrical current provided to fuse the cardiac tissue is provided at a relatively high frequency to create an RF energy field. The current and power can be varied and controlled in a myriad of manners, some of which are discussed later with reference to FIG. 3B. In a typical case, the power provided to fuse the tissue can have a value of about 30 watts, which can be returned via the (relatively small) return electrode 235 without burning the patient. The temperature of the cardiac tissue can be raised to from about 57° C. to about 100° C. to promote tissue fusing.

Figure 2D:
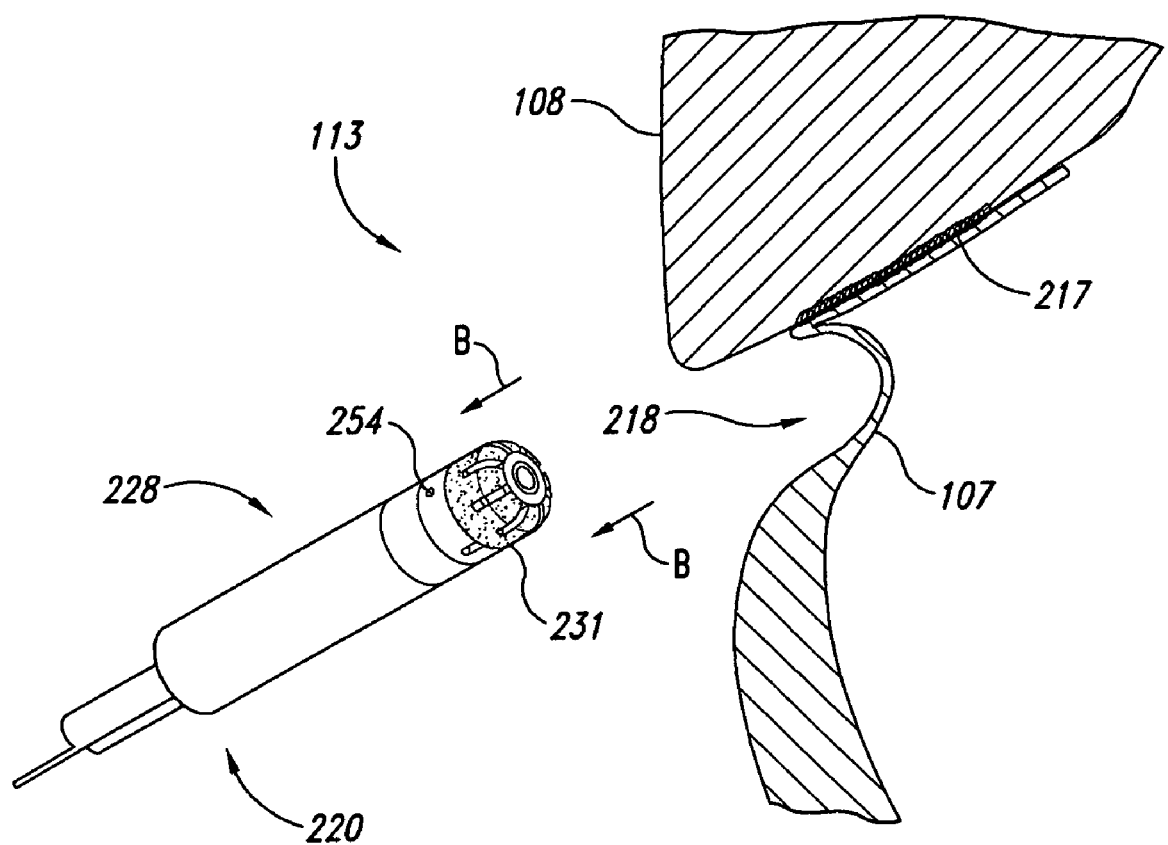

Referring now to FIG. 2D, the working portion 228 of the catheter 220 can be withdrawn from the PFO 113 (as indicated by arrows B) after the fusion process has been completed. The fusion process results in a seal 217 between the primum 107 and the secundum 108. The seal 217 is formed when, due to the elevated temperature resulting from the electrical field produced by the electrode 231, the cell walls of the cardiac tissue become disrupted. The tissue proteins, including collagen, are denatured. Intra- and inter-cellular fluids can accordingly mix, forming a type of "biological glue." The collagen in the cells also tends to shrink under heat, which can further act to bind the tissues together. The sealing process can be enhanced by coagulation of entrained blood, attachment of protein molecules, and/or cross-linking or entanglement of the collagen.

The seal 217 can be made to withstand significant pressures, at least approximately the same as the maximum pressures typically encountered between the left and right atria of the heart. For example, the seal 217 can withstand a pressure of about 5.0 mm Hg. The seal 217 need not extend for the entire length of the tunnel 112, which can be from about 5 mm to about 15 mm. In fact, in many cases, it may be desirable to leave the distal opening of the tunnel (e.g., the scupper valve, which opens into the left atrium) open. However, in many cases it is desirable to seal the entire width of the tunnel 112 (generally perpendicular to the plane of FIG. 2D), which can be from about 2 mm to about 18 mm. Accordingly, it may be desirable to have the flux lines 234 (FIG. 2C) extend widthwise as well as lengthwise into the tunnel 112. One way to achieve this end is to perfuse the region around the electrode 231 with conductive fluid, as described above, so as to increase the effective size of the electrode in the widthwise direction. In a particular embodiment, the power provided to the electrode 231 in combination with liquid perfusion and/or other factors causes the electrical field strength to be high enough to fuse the tissue at distances of at least 20% greater than the diameter of the catheter 220. In some situations, even if the seal 217 is initially incomplete, the body's own healing processes may act to complete the seal over time. Accordingly, the foregoing methods need not necessarily complete the entire seal during the surgical procedure.

After the catheter 220 is withdrawn from the sealed area, a small concavity 218 can remain in the right atrial septum. However, in light of the integrity of the seal 217, the concavity 218 can have little or no impact on the normal flow of blood from the right atrium 101 to the right ventricle. The integrity of the seal can be verified using any of a number of known techniques, including the use of contrast agents and/or bubbles.

FIGS. 3A-3C illustrate components of the catheter 220 described above with reference to FIGS. 2A-2D. FIG. 3A illustrates the manifold 253, FIG. 3B illustrates the electrode holder 270, and FIG. 3C illustrates the electrode 231 configured to be supported by the electrode holder 270. Referring to FIGS. 3A, 3B and 3C together, the manifold 253 can include a vacuum passage 355a that couples to the vacuum line 252. The vacuum passage 355a can also house the electrical lead 233 and the guide wire conduit 226, both of which are shown in FIG. 2C but are not shown in FIG. 3A for purposes of illustration. A fluid supply channel 363a extends axially through the manifold 253 and is coupleable at its distal end to the fluid supply line 262. At its proximal end, the fluid supply channel 363a feeds an annular fluid supply chamber 364 that is disposed annularly around the vacuum passage 355a and a vacuum recess 356.

The electrode holder 270 (FIG. 3B) includes a proximal portion 377 that is sealably received in the vacuum recess 356. The electrode holder 270 further includes multiple fluid supply channels 363b that extend through the electrode holder and align with the annular fluid supply chamber 364 of the manifold 253. A turning passage 375 receives a radially extending portion of the electrical lead (FIG. 2C) and turns it axially to be received by the electrode 231. A vacuum passage 355b aligns with the vacuum passage 355a of the manifold 253 (FIG. 3A).

The electrode 231 (FIG. 3C) includes an electrical lead passage 376 that receives the electrical lead from the turning passage 375 shown in FIG. 3B and provides for an electrical connection between the electrical lead and the electrode 231. The electrode 231 also includes fluid supply channels 363c that align with the corresponding fluid supply channels 363b of the electrode holder 270. Fluid provided to the fluid supply channels 363 exudes from the electrode 231 through the pores 261 in the electrode periphery 232. The vacuum ports 251 in the electrode 231 communicate with vacuum passage 355c and align with corresponding vacuum slots 357 in the electrode holder 270 (FIG. 3B) to provide a continuous vacuum path through the electrode 231, through the electrode holder 270, through the manifold 253, and to the vacuum line 252. The vacuum ports 251 can be relatively narrow to prevent excessive ingress by the (very flexible) primum while the vacuum is applied. For example, the vacuum ports 251 can have a width of less than about 0.020 inches in one embodiment, and can have other values in other embodiments. The shapes of the vacuum ports 251 can also be different in other embodiments. In any of these embodiments, the vacuum ports 251 can be spaced apart by 90° of arc or less (e.g., 45°) around the circumference of the electrode 231 so that all or substantially all the adjacent tissue is drawn toward the electrode 231.

The electrode holder 270 and the manifold 253 can be formed from a generally nonconductive material (e.g., a biocompatible plastic). The electrode 231 can be formed from a biocompatible conductive metal, such as bronze, copper, aluminum, silver, a platinum-iridium alloy, and/or other alloys. In a further aspect of this embodiment, the electrode 231 can be made from a sintered metal (e.g., sintered bronze) so as to have a generally porous configuration. Accordingly, the electrode 231 can pass the fluid supplied by the fluid supply system 260 to the region between adjacent portions of cardiac tissue. In another embodiment, the pores can be formed in the electrode 231 via a microdrilling processing, or another process that results in a distribution of relatively small openings.

As was also described above, the flow rate of the fluid through the porous electrode 231 can be selected to be high enough so as to prevent the adjacent cardiac tissue from adhering to the electrode 231, but not so high as to interfere with the vacuum forces drawing the cardiac tissue toward the electrode 231. In a particular embodiment, the flow resistance of the porous material comprising the electrode 231 can be such that the fluid supply system 260 (FIG. 2) provides at least 0.001 ml per minute of conducting fluid into the tissue, while about one bar of pressure is exerted by the tissue on the surface of the electrode 231 (under the influence of the vacuum system 250, FIG. 2B). In other embodiments, these parameters can have different values. The pores of the electrode 231 can be hydrophilic so that the surface tension of the saline or other supply fluid will not hinder movement of the fluid out to the adjacent tissue. Conversely, the surfaces of the vacuum ports 251 can be hydrophobic so as to keep the fluid adjacent to the porous portion of the electrode 231. These techniques, and/or other techniques that include selective application of hydrophobic and hydrophilic surface properties, can force the fluid to form the desired fluid layer that prevents or at least restricts sticking between the electrode 231 and the adjacent tissue. To provide a suitable flow of fluid, the electrode 231 can have a porosity of from about 1% to about 50%, and the flow rate of fluid through the electrode 231 can be varied by the fluid controller (and/or by the porosity of the electrode 231) to have a rate of from about 0.1 ml per minute up to about 10 ml per second. In other embodiments, these parameters can have other values. The resistance of the pores or other flow passages through the electrode 231 can be high enough that, in operation, the variation in flow rate per unit surface area from any one region to another is less than ten.

Figure 4A:
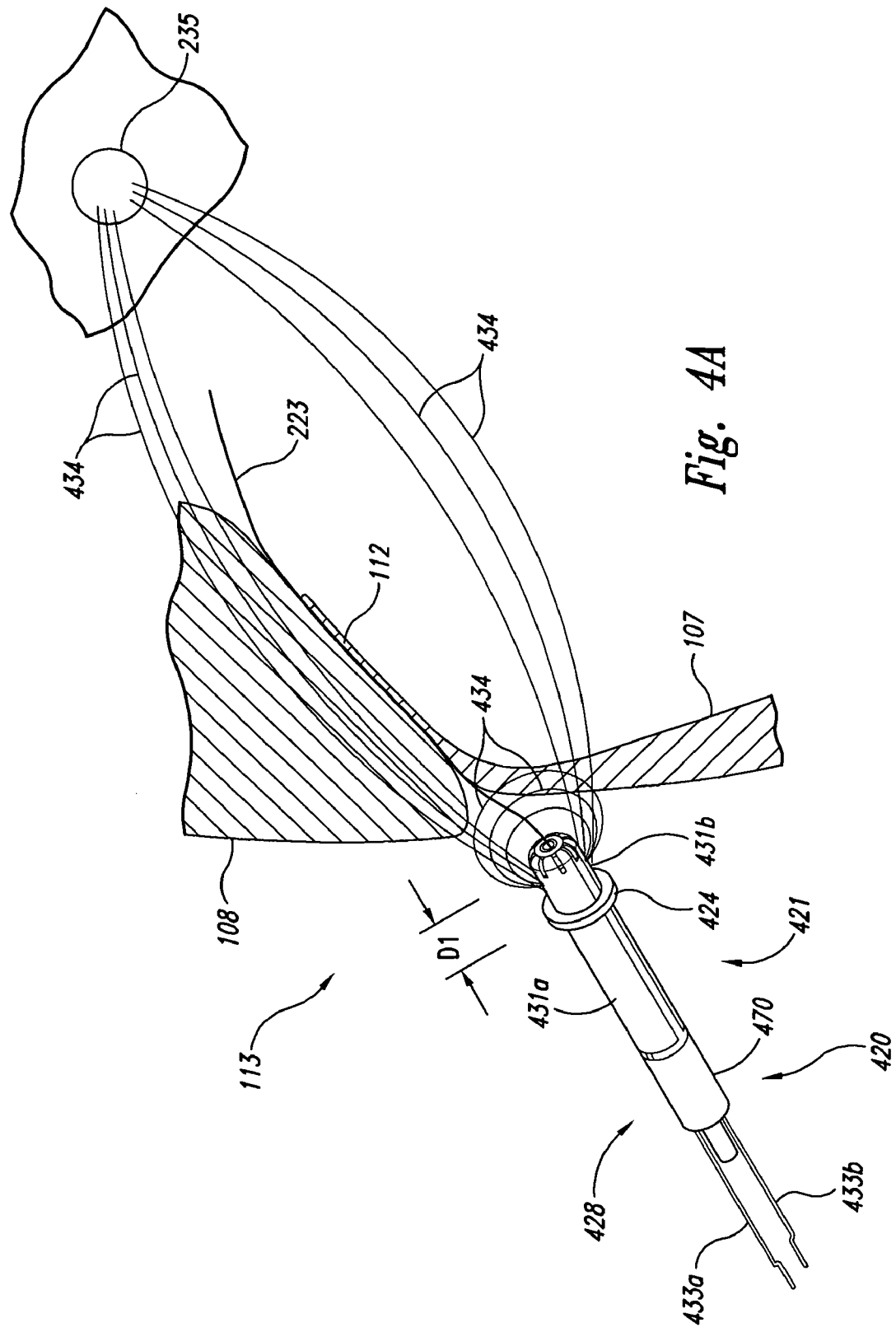
FIGS. 4A-4C illustrate a catheter having multiple electrodes and an inflatable collar in accordance with another embodiment of the invention.
Figure 4B:
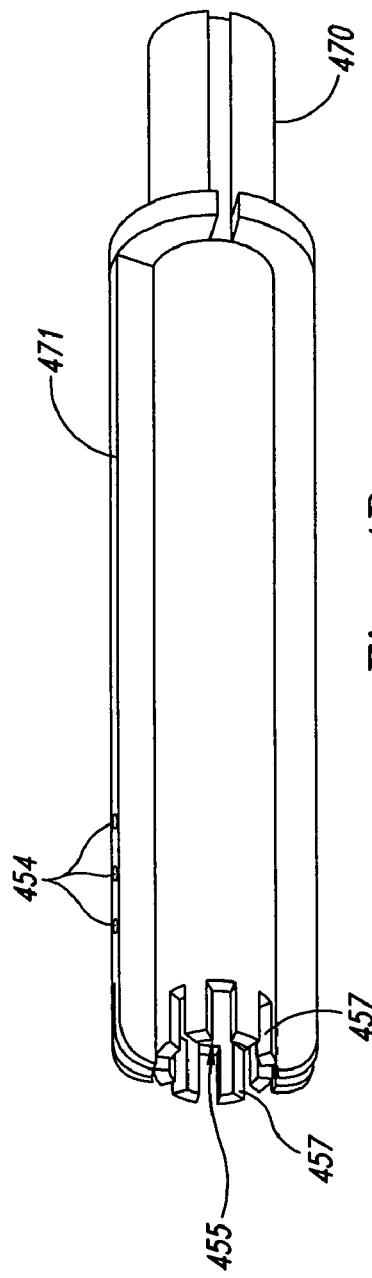
Figure 4C:
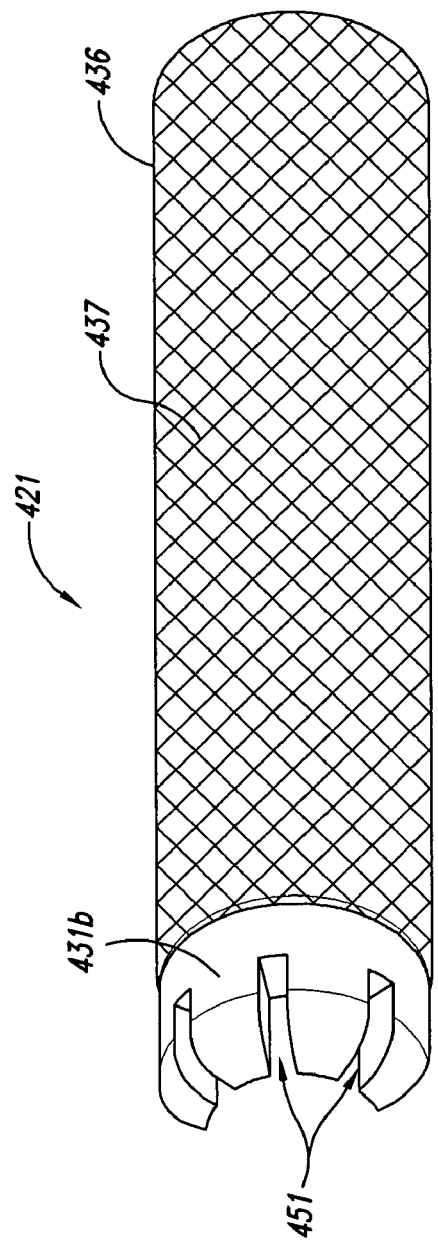

FIGS. 4A-4C illustrate components of a catheter 420 having a working portion 428 configured in accordance with another embodiment to the invention. In one aspect of this embodiment, the working portion 428 includes an electrode holder 470 configured to carry two electrodes 431 (shown as a first electrode 431a and a second electrode 431b). Each electrode 431 can be coupled to a corresponding lead 433a, 433b and can be configured to direct current in a bipolar manner during fusion of the primum 107 and the secundum 108. The spacing between adjacent electrodes can be selected to avoid sparking (which can damage the adjacent cardiac tissue) at anticipated power levels.

In one embodiment, the return electrode 235 described above with reference to FIG. 2C need not be provided during use of the catheter 420. However, in another embodiment, the return electrode 235 can be used even with the bipolar electrodes 431a, 431b. Accordingly, the resulting flux lines 434 can include lines (a) extending between the bipolar electrodes 431a, 431b and (b) between each bipolar electrode 431 and the return electrode 235. The bipolar/monopolar arrangement is expected to provide additional benefits in that the bipolar portion of the field can provide for good short-range tissue sealing (close to the electrodes 431), and the monopolar portions of the field can provide for good long-range tissue sealing (further away from the electrodes 431).

The catheter 420 can also include an inflatable collar 424 or other device positioned a selected distance D1 from the distal tip (e.g., from about 1 mm to about 15 mm). Once the catheter 420 has been introduced into the right atrium 101, the inflatable collar 424 can be inflated (e.g., with saline) so as to locally increase an effective diameter of the distal end 421 of the catheter 420. For example, the local diameter can be increased from a nominal value of 5 millimeters to value of 10 millimeters or more. When the catheter 420 is advanced along the guide wire 223, the inflatable collar 424 can contact the secundum 108 and the primum 107 at the point where the catheter 420 extends into the tunnel 112 by the selected distance D1. Accordingly, the inflatable collar 424 can act as a locating device to ensure that the catheter 420 is inserted into the tunnel 112 by the correct distance. The inflatable collar 424 can also seal against the surfaces of the primum 107 and the secundum 108 facing outwardly into the right atrium 101. Accordingly, the inflatable collar 424 can help to secure the working portion 428 of the catheter 420 at the PFO 113. This function may be particularly useful when it is difficult to seal the catheter 420 against the internal surfaces of the tunnel 112, for example, when the tunnel 112 is relatively short. In a further particular aspect of this embodiment, the inflatable collar 424 can be inflated with a contrast medium (e.g., a radiopaque contrast medium) configured to enhance visualization of the collar 424 by fluoroscopic, ultrasonic or other techniques. The visualization technique can be used to increase the accuracy with which the catheter 420 is positioned relative to the tunnel 112.

FIGS. 4B and 4C illustrate the electrode holder 470 and the second electrode 431b, respectively, of the catheter 420 described above. The electrode holder 470 can include an intermediate ridge 471 positioned between the second electrode 431b and the opposing first electrode 431a (FIG. 4A). The electrode holder 470 can also include vacuum slots 457 configured to align with corresponding vacuum ports 451 of the electrode 431b. A central vacuum passage 455 can be located axially along the centerline of the electrode holder 470 to conduct away fluid evacuated from the distal end 421 of the catheter 420 for securing the catheter and/or drawing cardiac tissue together, as described above.

In other embodiments, devices other than the collar 424 can be used to locate the catheter 420 within the PFO 113. For example, as described above with reference to FIGS. 2A-2D, the collar 424 can be eliminated, and the suction drawn by the catheter 220 (via the vacuum ports 251 and the single locating port 254) on the adjacent cardiac tissue can serve to properly locate the catheter within the PFO 113. In other embodiments, the catheter 420 can be outfitted with a series of axial locating ports 454 extending from a region proximate to the distal tip, along the length of the catheter 420. Each locating port 454 can be separately monitored so that when the port 454 corresponding to the desired penetration depth of the catheter 420 within the PFO 113 is closed, the practitioner can cease advancing the catheter 420 through the PFO 113.

In one embodiment, the electrode 431b shown in FIG. 4C can be porous and can accordingly be supplied with fluid to resist sticking between the electrode 431b and the adjacent cardiac tissue. In another embodiment, shown in FIG. 4C, the electrode 431b need not include provisions for receiving such fluid, and can instead be positioned in close thermal contact with a heat sink 436. An insulating layer 437 can be positioned between the electrode 431b and the heat sink 436, and can also be positioned around the heat sink 436. In a particular aspect of this embodiment, the insulating layer 437 can include a material that is electrically insulating (so as not to transmit electrical signals to the heat sink 436), but also thermally conductive (so as to efficiently transmit heat to the heat sink 436). Suitable insulating materials include thin (e.g., 0.0005 inch thick) Teflon. In a still further embodiment, the electrode 431b can include pores or other fluid delivery passages in addition to the insulating layer 437 and the heat sink 436. The electrode 431b can also be coated with a biocompatible, anti-stick material, including a conductive grease or hydrogel.

Figure 5:
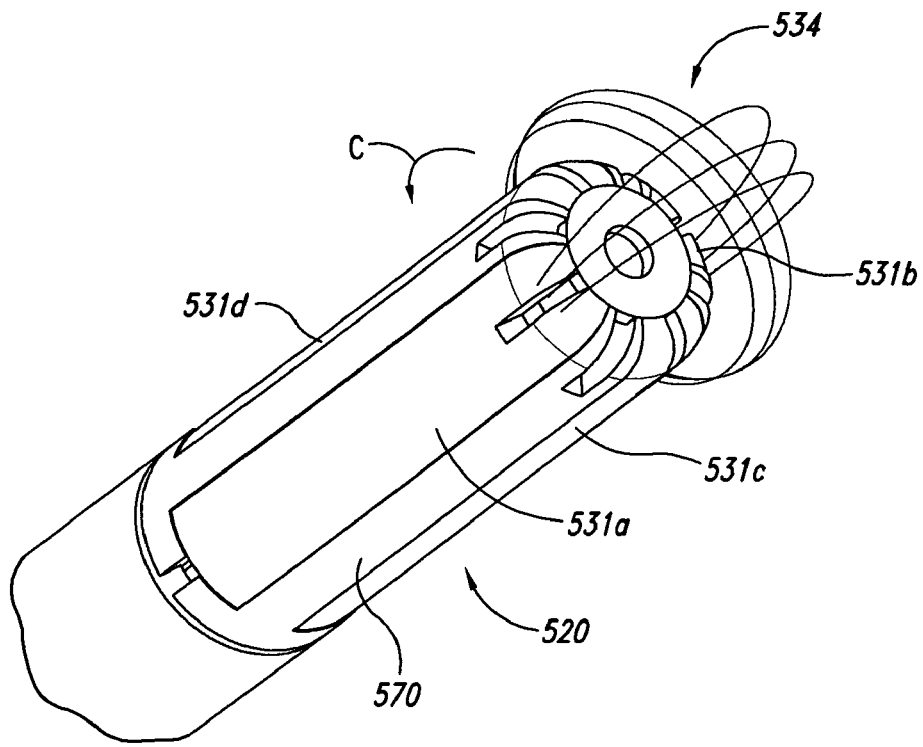
FIG. 5 illustrates a catheter having multiple electrodes configured to operate in a phased manner in accordance with still another embodiment of the invention.

FIG. 5 illustrates a catheter 520 having an electrode holder 570 configured to support four electrodes 531a-531d in accordance with another embodiment of the invention. In a particular aspect of this embodiment, opposing pairs of electrodes (e.g., electrodes 531a-531b and electrodes 531c-531d) are coupled to form bipolar pairs. The current provided to each pair of electrodes can also be phase shifted, for example, in a phase quadrature manner. As a result, the field (represented by flux lines 534) provided by the electrodes 531 will tend to rotate around the electrode holder 570, as indicated by arrow C. A feature of this arrangement is that it can create a rotationally polarized, omnidirectional field. One advantage of this feature is that the omnidirectional field can eliminate the need for orienting the catheter to a specific rotational position around its longitudinal axis. Another advantage is that the omnidirectional field represents an effectively increased "electrical" diameter of the catheter 520. For example, energizing electrodes spaced 180° from each other can make maximum use of the available catheter diameter and extend the "reach" of the bipolar electrical field. The omnidirectional, large diameter field can more effectively and uniformly fuse the adjacent cardiac tissue.

The signal provided to the electrodes 531 or any of the electrodes described above can vary in any number of suitable manners. In particular embodiments, the signal can be generally sinusoidal to provide a smooth and continuously varying transition in current. In other embodiments, the signal can vary in other manners (e.g., a square wave or triangular wave). The frequency of the signal can have a value of at least 10 kHz, the point at which a neuro-muscular response to the signal is typically attenuated. In a particular aspect of these embodiments, the crest factor (ratio of peak voltage to rms voltage) can be less than about 5. Keeping the crest factor below this value can reduce the likelihood of sparking, which can inhibit tissue bonding. The power provided by the electrical signal can be contoured (e.g., varied) as a function of time and/or tissue impedance to account for changes in the electrical characteristics of the tissue over the course of the welding process. These changes can include an increase in tissue impedance as the tissue is heated.

Figure 6A:
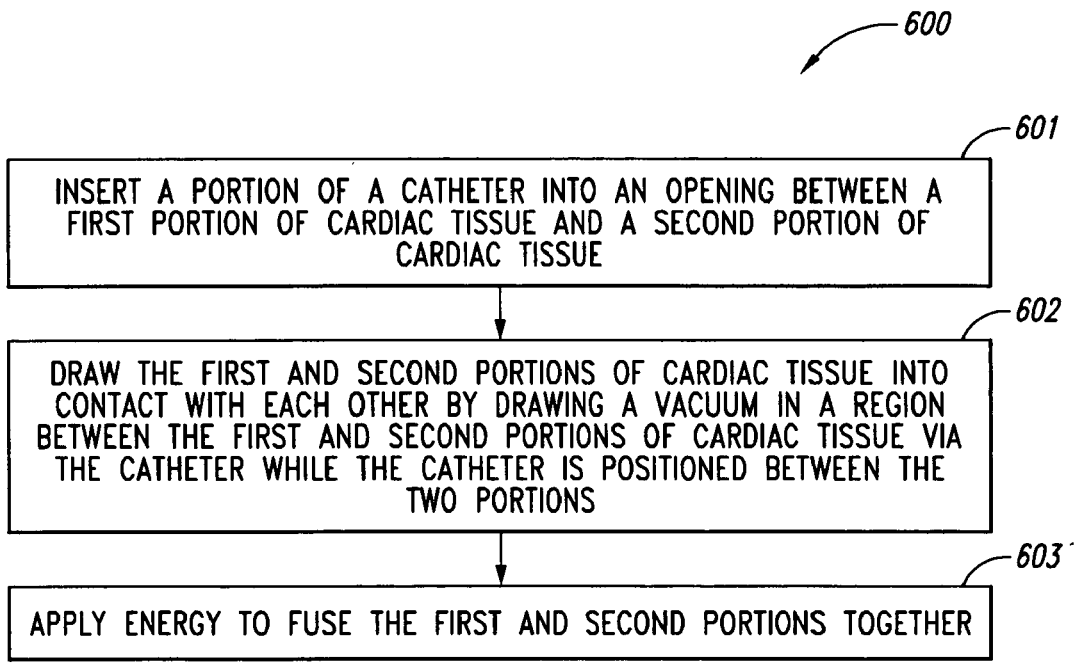
FIGS. 6A-6B illustrate methods for treating cardiac tissue in accordance with further embodiments of the invention.
Figure 6B:
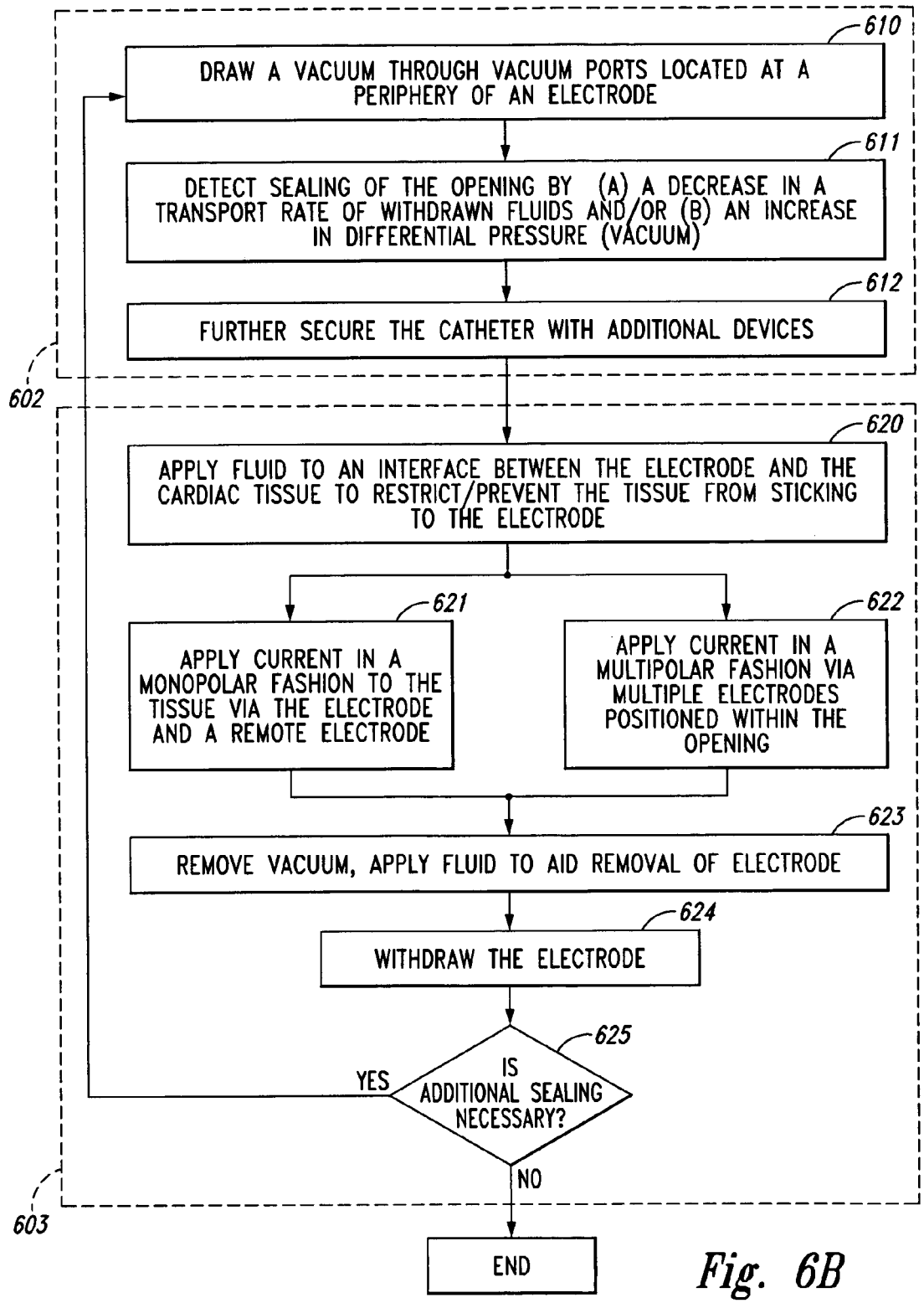

FIGS. 6A-6B illustrate methods for treating cardiac tissue in accordance with several embodiments of the invention. Referring first to FIG. 6A, a process 600 includes inserting a portion of the catheter into an opening between a first portion of cardiac tissue and a second portion of cardiac tissue (process portion 601). The portions of cardiac tissue can include the primum and secundum, as discussed above, or other portions of cardiac tissue that may have an opening formed between them. In process portion 602, the process includes drawing the first and second portions of cardiac tissue into contact with each other by drawing a vacuum in a region between the first and second portions of cardiac tissue. This process is performed via the catheter while the catheter is positioned between the two portions. For example, the process can be performed while the catheter is positioned in the tunnel portion of a PFO. In process portion 603, energy can be applied to the first and second portions to fuse the first and second portions together.

FIG. 6B illustrates further details of process portions 602 and 603, performed in accordance with particular embodiments of the invention. For example, process portion 602 can include drawing a vacuum through vacuum ports located at a periphery of an electrode (process portion 610). In process portion 611, the process can include detecting sealing of the opening via (a) a decrease in the transport rate of withdrawn fluids and/or (b) an increase in the differential pressure (vacuum). The catheter can further be secured and sealed with additional devices (e.g., an inflatable collar) in optional process portion 612.

Process portion 603 can include applying fluid to an interface between the electrode and an adjacent cardiac tissue to restrict and/or prevent tissue from sticking to the electrode (process portion 620). In one embodiment, the current can be applied in a monopolar fashion to the tissue via the electrode and a remote electrode (process portion 621). In another embodiment, the current can be applied in a multipolar fashion via multiple electrodes positioned within the opening (process portion 622). As described above with reference to FIG. 4A, the current can also be applied in both a monopolar and bipolar fashion simultaneously. After the current has been applied and at least a portion of the opening has been sealed, the vacuum applied in process portion 610 can be removed (process portion 623). Optionally, the fluid applied in process portion 620 can remain applied (or can be restarted if the flow was halted for any reason) to aid in removing the electrode. For example, applying the fluid at this point may assist in detaching tissue that might have attached to the electrode during the application of current from the electrode. The electrode can then be withdrawn (process portion 624). If the opening is particularly large, the process can include determining whether additional sealing is necessary (process portion 625). If so, the process can return to process portion 610. If not, the process can end.

In other embodiments, some or all of the foregoing steps can be used to seal openings in cardiac tissue that are not necessarily associated with a PFO. For example, such methods can be used to close other naturally occurring cardiac openings, e.g., a patent ductus arteriosis (PDA) or a left atrial appendage, and/or openings in blood vessels or other cardiovascular tissue. In still further embodiments, these techniques can be used to close openings deliberately created during surgical procedures. The methods described above for sealing these openings can be supplemented by or replaced by other methods (e.g., laser heating, direct heat, and/or meltable adhesives), all of which can be made more effective by the vacuum drawn from within the opening.

In still further embodiments, the tissue can be shrunk to the point that the opening tends to open only under pressures higher than those under which it would otherwise open, but the tissue need not necessarily be sealed. For example, in the case of a PFO, the primum can be shrunk (without necessarily welding it to the secundum) so that the pressure required to open the corresponding tunnel is elevated from what it would otherwise be in the absence of shrinkage. This procedure can be used to prevent interatrial blood flow completely, or prevent such flow at all but relatively high interatrial pressures. This procedure can be performed with or without the use of vacuum, with or without the use of exuded fluid, and via RF energy or any other energy (e.g., direct heat, microwave or laser energy) that shrinks the primum or other target tissue.

One feature of several catheter embodiments described above is that they can include proximal ends deliberately sized to be placed within an opening between adjacent portions of cardiac tissue. An advantage of this feature is that it places an energy transmitter (e.g., an electrode) carried by the catheter into close contact with the cardiac tissue. Accordingly, the energy transmitter can provide high current density in a local region (where it is needed for fusing) without heating up large volumes of adjacent tissue, which can be damaging. The vacuum system, also carried by the catheter, can be used to further draw the tissue portions together from a position between the tissue portions. Another advantage associated with the size and vacuum capability of the catheter is that both features can be used to (a) detect proper positioning of the catheter, and/or (b) secure the catheter in place.

Still another feature of several catheter embodiments described above is that they can include fluid supply systems that provide a thin conductive fluid layer between the electrode and the adjacent cardiac tissue. An advantage of this feature is that it can reduce the likelihood for the cardiac tissue portions to fuse to the electrode as they are fused to each other. Accordingly, this feature can produce tissue welds having greater integrities than are available with conventional catheters.

Still another feature of at least several of the foregoing embodiments is that they can include one or more electrodes that deliver RF energy into the tissues surrounding the opening that is to be fused. An advantage of this arrangement is that the RF energy can be projected beyond the physical boundaries of the electrodes with relative ease. Another advantage of this feature is that many of the parameters that determine the nature and the extent of the seal formed by the RF energy can be controlled in situ by varying the current or voltage applied to the electrodes.

Yet another feature of embodiments described above is that they seal the cardiac tissue without leaving behind an implanted device. An advantage of this feature is that the resulting seal will not fail due to movement of such a device. Furthermore, such devices may be undesirable, as they can become dislodged, and/or weaken, erode or tear the cardiac tissue, and/or cause adverse cardiac responses. Still further, such implanted devices may preclude future percutaneous left atrial procedures that require a transseptal puncture of the interatrial septum at the primum. Representative procedures having this requirement include the placement of percutaneous heart valves and/or electrophysiology mapping and ablation catheters in the left atrium, and the placement of left atrial appendage devices. Eliminating such devices eliminates these potential adverse results.

From the foregoing, it will be appreciated that specific embodiments of the invention have been described herein for purposes of illustration, but that various modifications may be made without deviating from the spirit and scope of the invention. For example, in one embodiment, the guide wire 223 can remain in place during tissue welding and can function as an electrode to enhance the delivery of electrical energy to the cardiac tissue. Aspects of the invention described in the context of particular embodiments may be combined or eliminated in other embodiments. For example, the catheter 220 shown in FIG. 2A can include the collar 424 shown in FIG. 4A. Although advantages associated with certain embodiments of the invention have been described in the context of those embodiments, other embodiments may also exhibit such advantages. Additionally, none of the foregoing embodiments need necessarily exhibit such advantages to fall within the scope of the invention. Accordingly, the invention is not limited except as by the appended claims.

We claim:

1. A device for treating cardiovascular tissue, comprising:
   a catheter having a proximal end and a distal end;
   an energy transmitter positioned toward the distal end of the catheter and being laterally fixed relative to the catheter, the energy transmitter being configured to be received in an opening between a first portion of cardiovascular tissue and a second portion of cardiovascular tissue, the energy transmitter being coupleable to an energy source to fuse the first and second portions of the cardiovascular tissue while the energy transmitter is positioned in the opening; and
   a vacuum passage positioned in the catheter and having at least one port positioned to be received in the opening to draw the first and second portions of the cardiac tissue into contact with each other, the vacuum passage being coupleable to a vacuum source.

2. The device of claim 1 wherein the energy transmitter includes at least one electrode coupleable to a source of electrical power.

3. The device of claim 1 wherein the energy transmitter includes at least one electrode coupleable to a source of electrical power, and wherein the at least one electrode is configured to heat tissue at an interface between a primum and a secundum of the heart to attach the primum to the secundum.

4. The device of claim 1 wherein the energy transmitter includes at least one electrode coupleable to a source of electrical power, and wherein the device further comprises a return electrode that is coupleable to a patient at a location superior to the at least one electrode.

5. The device of claim 1 wherein the energy transmitter includes at least one electrode coupleable to a source of electrical power, and wherein the device further comprises a return electrode that is coupleable to a patient at a location superior to the heart.

6. The device of claim 1 wherein the energy transmitter includes at least one electrode coupleable to a source of electrical power, and wherein the device further comprises a return electrode that is coupleable to a patient at a location remote from the at least one electrode.

7. The device of claim 1 wherein the energy transmitter includes a first electrode and a second electrode proximate to the first electrode, and wherein the first and second electrodes are configured to be coupled to different electrical potentials.

8. The device of claim 1 wherein the energy transmitter includes a first electrode, a second electrode proximate to the first electrode, and a return electrode coupleable to a patient at a location remote from the first and second electrodes, and wherein the first and second electrodes are configured to be coupled to different electrical potentials to transmit a bipolar signal between them, and wherein the first and second electrodes are each configured to transmit a monopolar signal to the return electrode.

9. The device of claim 1 wherein the energy transmitter includes two pairs of electrodes with each pair configured to transmit a bipolar signal.

10. The device of claim 1 wherein the energy transmitter includes two pairs of electrodes coupled to an electrical power source to provide a phase quadrature waveform to the first and second pairs of electrodes.

11. The device of claim 1 wherein the energy transmitter includes a plurality of electrodes arranged circumferentially around a periphery of the distal end of the catheter.

12. The device of claim 1, further comprising an inflatable chamber positioned proximate to the distal end of the catheter, the inflatable chamber having an inflated dimension larger than a corresponding dimension of the opening between the first and second portions of the cardiac tissue.

13. The device of claim 12 wherein the inflatable chamber is coupleable to a source of visualization fluid to increase visibility of the inflatable chamber when it is inflated.

14. The device of claim 1 wherein the catheter is elongated along an axis and wherein the distal portion of the catheter includes a peripheral portion disposed radially outwardly from the axis, and wherein the at least one port includes a plurality of ports positioned circumferentially around the peripheral portion.

15. The device of claim 1 wherein the at least one port has a width of about 0.020 inches or less.

16. The device of claim 1 wherein the at least one port includes a plurality of ports spaced apart by 90 degrees of arc or less around the distal end of the catheter.

17. The device of claim 1 wherein the vacuum passage is coupleable to a variable vacuum source.

18. The device of claim 1 wherein the at least one port includes a first port proximate to a distal tip of the catheter and a second port positioned spaced axially apart from the first port, the second port being spaced apart from the distal tip by a distance approximately equal to a target penetration distance of the catheter into the opening.

19. The device of claim 1 wherein the catheter is elongated along an axis and wherein the distal portion of the catheter has a diameter of about 5 millimeters or less relative to the axis.

20. The device of claim 1, further comprising an inflatable chamber positioned proximate to the distal end of the catheter, and wherein the distal portion of the catheter has a diameter of about 5 millimeters or less when the chamber is deflated, and a diameter of 10 millimeters or more when the chamber is inflated.

21. The device of claim 1 wherein the catheter is elongated along an axis and wherein the distal portion of the catheter has a diameter of about 4 millimeters.

22. The device of claim 1 wherein the energy transmitter is configured to at least inhibit sticking of the tissue to the energy transmitter.

23. The device of claim 1 wherein the catheter includes a plurality of openings coupleable to a source of fluid, the openings being sized to exude fluid while the catheter is positioned in the opening between the first and second portions of the cardiovascular tissue.

24. The device of claim 1 wherein the energy transmitter includes an electrode having a plurality of openings coupleable to a source of fluid, the openings being sized to exude fluid while the catheter is positioned in the opening between the first and second portions of the cardiovascular tissue.

25. The device of claim 1 wherein the energy transmitter includes an electrode having a plurality of openings coupleable to a source of fluid, the openings being sized to exude fluid while the catheter is positioned in the opening between the first and second portions of the cardiac tissue, and wherein at least a portion of the catheter has a liquid impervious material positioned to direct the fluid to an interface between the at least one electrode and the tissue portions, and further wherein the at least one port is located in the electrode at least proximate to the openings.

26. The device of claim 1 wherein the energy transmitter includes at least one electrode, and wherein the device further comprises at least one monitor operatively coupled to the at least one electrode to monitor at least one of a current transmitted by the at least one electrode, a voltage applied by the at least one electrode, and an impedance of an electrical circuit that includes the at least one electrode.

27. The device of claim 1, further comprising at least one monitor operatively coupled to the catheter and configured to monitor at least one of a flow rate of fluid drawn through the vacuum passage, a differential pressure drawn through the vacuum passage, and a temperature of a region at least adjacent to the distal end of the catheter.

28. The device of claim 1 wherein the catheter includes no components configured to be left in the patient after fusing the first and second portions of cardiac tissue.

29. The device of claim 1 wherein the catheter includes a guide wire channel configured to slideably receive a guide wire along which the catheter is configured to move.

30. The device of claim 1 wherein the catheter includes a flexible section located between the proximal and distal ends, the flexible section being configured to flex while the distal end is secured to the first and second portions of cardiovascular tissue and the heart beats.

31. A device for repairing a patent foramen ovale, comprising:
a catheter having a proximal end, a distal end, and a working portion proximate to the distal end;
at least one electrode carried by the working portion of the catheter and being laterally fixed relative to the catheter, the electrode being configured to be received in a patency between a primum and secundum of a patient's heart, the electrode being coupleable to an electrical power source to fuse the primum and secundum while the electrode is positioned in the patency, the electrode having at least one vacuum port and at least one fluid delivery opening;

a vacuum passage carried by the working portion of the catheter and coupled to the vacuum port, the vacuum passage being coupleable to a vacuum source to draw the primum and secundum together; and at least one fluid supply channel carried by the working portion and coupled to the at least one fluid delivery opening, the at least one fluid supply channel being coupleable to a source of fluid to at least restrict sticking between the electrode and at least one of the primum and the secundum.

32. The device of claim 31 wherein the electrode is at least partially porous, and wherein the at least one fluid delivery opening includes a pore of the electrode.

33. The device of claim 31 wherein the electrode is porous and wherein the liquid flow rate per unit area of the electrode at any point on the electrode does not vary by more than a factor of ten relative to the liquid flow rate per unit area of any other portion of the electrode.

34. A device for treating cardiac tissue, comprising:
energy transmission means for fusing cardiac tissue portions;
insertion means for inserting the energy transmission means into an opening between the cardiac tissue portions, wherein the energy transmission means is laterally fixed relative to the insertion means; and
vacuum means for drawing a vacuum from within the opening between the cardiac tissue portions, the vacuum means being configured to be positioned within the opening while drawing the vacuum.

35. The device of claim 34, further comprising fluid supply means for supplying fluid into the opening while the vacuum means draws a vacuum.

36. The device of claim 34 wherein the energy transmission means includes at least one electrode.

37. The device of claim 34 wherein the energy transmission means includes at least one porous electrode having pores configured to supply a fluid to the opening while the vacuum means draws a vacuum, and wherein the vacuum means includes a plurality of vacuum ports positioned circumferentially around a peripheral surface of the porous electrode.

* * * * *